US00RE47148E

(19) United States
(12) Reissued Patent
Rhad et al.

(10) Patent Number: US RE47,148 E
(45) Date of Reissued Patent: Dec. 4, 2018

(54) HANDHELD BIOPSY DEVICE WITH NEEDLE FIRING

(71) Applicant: DEVICOR MEDICAL PRODUCTS, INC., Cincinnati, OH (US)

(72) Inventors: Edward A. Rhad, Fairfield, OH (US); John A. Hibner, Mason, OH (US); Harold W. Craig, Johns Creek, GA (US); Richard P. Nuchols, Williamsburg, OH (US)

(73) Assignee: Devicor Medical Products, Inc., Cincinnati, OH (US)

(21) Appl. No.: 15/198,313

(22) Filed: Jun. 30, 2016

Related U.S. Patent Documents

Reissue of:
(64) Patent No.: 8,764,680
Issued: Jul. 1, 2014
Appl. No.: 12/953,715
Filed: Nov. 24, 2010

U.S. Applications:
(60) Provisional application No. 61/408,795, filed on Nov. 1, 2010.

(51) Int. Cl.
*A61B 10/00* (2006.01)
*A61B 10/02* (2006.01)

(52) U.S. Cl.
CPC ..... *A61B 10/0266* (2013.01); *A61B 10/0275* (2013.01); *A61B 10/0283* (2013.01); *A61B 2010/0208* (2013.01)

(58) Field of Classification Search
CPC ..... A61B 2010/0208; A61B 10/0275
(Continued)

(56) References Cited

U.S. PATENT DOCUMENTS 5,526,822 A 6/1996 Burbank et al.
5,779,647 A * 7/1998 Chau ..... A61B 10/0275 600/564

(Continued)

FOREIGN PATENT DOCUMENTS

CN 1700887 A 11/2005
CN 101548898 A 10/2009

(Continued)

OTHER PUBLICATIONS

Australian Office Action dated May 21, 2015 for Application No. AU 2011323906, 4 pgs.

(Continued)

*Primary Examiner* — Cary E Wehner
(74) *Attorney, Agent, or Firm* — Frost Brown Todd LLC

(57) ABSTRACT

A biopsy device includes a body, a needle, and a cutter. A motor is operable to both move the cutter relative to the needle and actuate a needle firing assembly to retract and fire the needle relative to the body. The biopsy device also includes a needle rotation assembly that is configured to substantially prevent rotation of the needle about the longitudinal axis when the needle is in a proximal position yet permit rotation of the needle about the longitudinal axis when the needle is in a distal position. A valve assembly of the biopsy device includes a slider that selectively couples a secondary lumen in the needle with either atmospheric air or saline based on the longitudinal position of the slider. The cutter passes through the slider.

35 Claims, 29 Drawing Sheets

(58) Field of Classification Search
USPC ..... 600/562–568
See application file for complete search history.

(56) References Cited

U.S. PATENT DOCUMENTS

| | | | | |
|---|---|---|---|---|
| 6,086,544 | A | 7/2000 | Hibner et al. | |
| 6,626,849 | B2 | 9/2003 | Huitema et al. | |
| 7,442,171 | B2 | 10/2008 | Stephens et al. | |
| 7,517,322 | B2 | 4/2009 | Weikel, Jr. et al. | |
| 7,854,706 | B2 | 12/2010 | Hibner | |
| 7,854,707 | B2 | 12/2010 | Hibner et al. | |
| 7,918,804 | B2 | 4/2011 | Monson et al. | |
| 8,057,402 | B2 | 11/2011 | Hibner et al. | |
| 8,109,885 | B2 | 2/2012 | Heske et al. | |
| 8,162,852 | B2 | 4/2012 | Norris | |
| 8,167,815 | B2 | 5/2012 | Parihar | |
| 8,172,773 | B2 | 5/2012 | Heske et al. | |
| 8,192,369 | B2 | 6/2012 | Bacon et al. | |
| 8,206,316 | B2 | 6/2012 | Hibner et al. | |
| 8,241,226 | B2 | 8/2012 | Hibner et al. | |
| 8,251,916 | B2 | 8/2012 | Speeg | |
| 8,277,394 | B2 | 10/2012 | Hibner | |
| 8,376,957 | B2 | 2/2013 | Hibner et al. | |
| 8,480,595 | B2 | 7/2013 | Speeg et al. | |
| 8,672,860 | B2 | 3/2014 | Moore et al. | |
| 8,702,623 | B2 | 4/2014 | Parihar et al. | |
| 8,764,680 | B2 | 7/2014 | Rhad et al. | |
| 8,858,465 | B2 | 10/2014 | Fiebig | |
| 9,345,457 | B2 | 5/2016 | Speeg et al. | |
| 2005/0054947 | A1* | 3/2005 | Goldenberg | A61B 10/0233 600/567 |
| 2006/0074345 | A1 | 4/2006 | Hibner | |
| 2007/0032742 | A1 | 2/2007 | Monson et al. | |
| 2008/0195066 | A1 | 8/2008 | Speeg et al. | |
| 2008/0200836 | A1* | 8/2008 | Speeg et al. | 600/567 |
| 2008/0214955 | A1 | 9/2008 | Speeg et al. | |
| 2009/0171243 | A1 | 7/2009 | Hibner et al. | |
| 2009/0299221 | A1* | 12/2009 | Bacon et al. | A61B 10/0275 600/567 |
| 2010/0106056 | A1 | 4/2010 | Norris | |
| 2010/0113973 | A1* | 5/2010 | Hibner et al. | 600/567 |
| 2010/0152610 | A1 | 6/2010 | Parihar et al. | |
| 2010/0160819 | A1 | 6/2010 | Parihar et al. | |
| 2010/0160824 | A1 | 6/2010 | Parihar et al. | |
| 2010/0292607 | A1 | 11/2010 | Moore et al. | |
| 2010/0317997 | A1 | 12/2010 | Hibner et al. | |
| 2011/0208090 | A1 | 8/2011 | Parihar | |
| 2012/0059247 | A1 | 3/2012 | Speeg et al. | |
| 2012/0265095 | A1 | 10/2012 | Fiebig | |

FOREIGN PATENT DOCUMENTS

| | | | |
|---|---|---|---|
| CN | 103281970 | A | 9/2013 |
| EP | 2062537 | A1 | 5/2009 |
| EP | 2062538 | | 5/2009 |
| EP | 2062538 | A1 | 5/2009 |
| EP | 2135558 | A1 | 12/2009 |
| JP | 2004-235837 | A | 12/2004 |
| JP | 2009-160384 | A | 7/2009 |
| JP | 2010-000353 | A | 1/2010 |
| JP | 5859555 | B2 | 2/2016 |
| MX | 2013004893 | A | 10/2013 |
| WO | WO 2002/41797 | A1 | 5/2002 |
| WO | WO 2006/005342 | | 1/2006 |
| WO | WO 2011/019343 | * | 2/2011 |

OTHER PUBLICATIONS

Chinese Office Action dated Aug. 26, 2014 for Application No. CN 201180063684.4, 9 pgs.
Chinese Office Action dated Jan. 21, 2015 for Application No. CN 201180063684.4, 6 pgs.
Chinese Office Action dated May 18, 2015 for Application No. CN 201180063684.4, 7 pgs.
International Search Report dated May 25, 2012 for Application No. PCT/US2011/054892, 1 pg.
International Preliminary Report on Patentability and Written Opinion dated May 7, 2013 for Application No. PCT/US2011/054892, 4 pgs.
Japanese Office Action dated Jun. 30, 2015 for Application No. JP 2013-536645, 2 pgs.
Mexican Office Action dated May 12, 2015 for Application No. MX/a/2013/004893, 4 pgs.
Supplementary European Search Report and Written Opinion dated Sep. 16, 2014 for Application No. EP 11838420.5, 7 pgs.
U.S. Appl. No. 61/408,795, filed Nov. 1, 2010.
Korean Office Action, Notification of Reason for Refusal, dated Oct. 4, 2018 for Application No. KR 10-2018-7016810, 5 pgs.
U.S. Appl. No. 61/381,466, filed Sep. 10, 2010, Hibner.
U.S. Appl. No. 12/542,775, filed Aug. 18, 2009, Hibner.
U.S. Appl. No. 12/709,624, filed Feb. 22, 2010, Parihar.
U.S. Appl. No. 12/709,695, filed Feb. 22, 2010, Hibner et al.
International Search Report dated May 25, 2012 for Application No. PCT/US2011/054892.

* cited by examiner

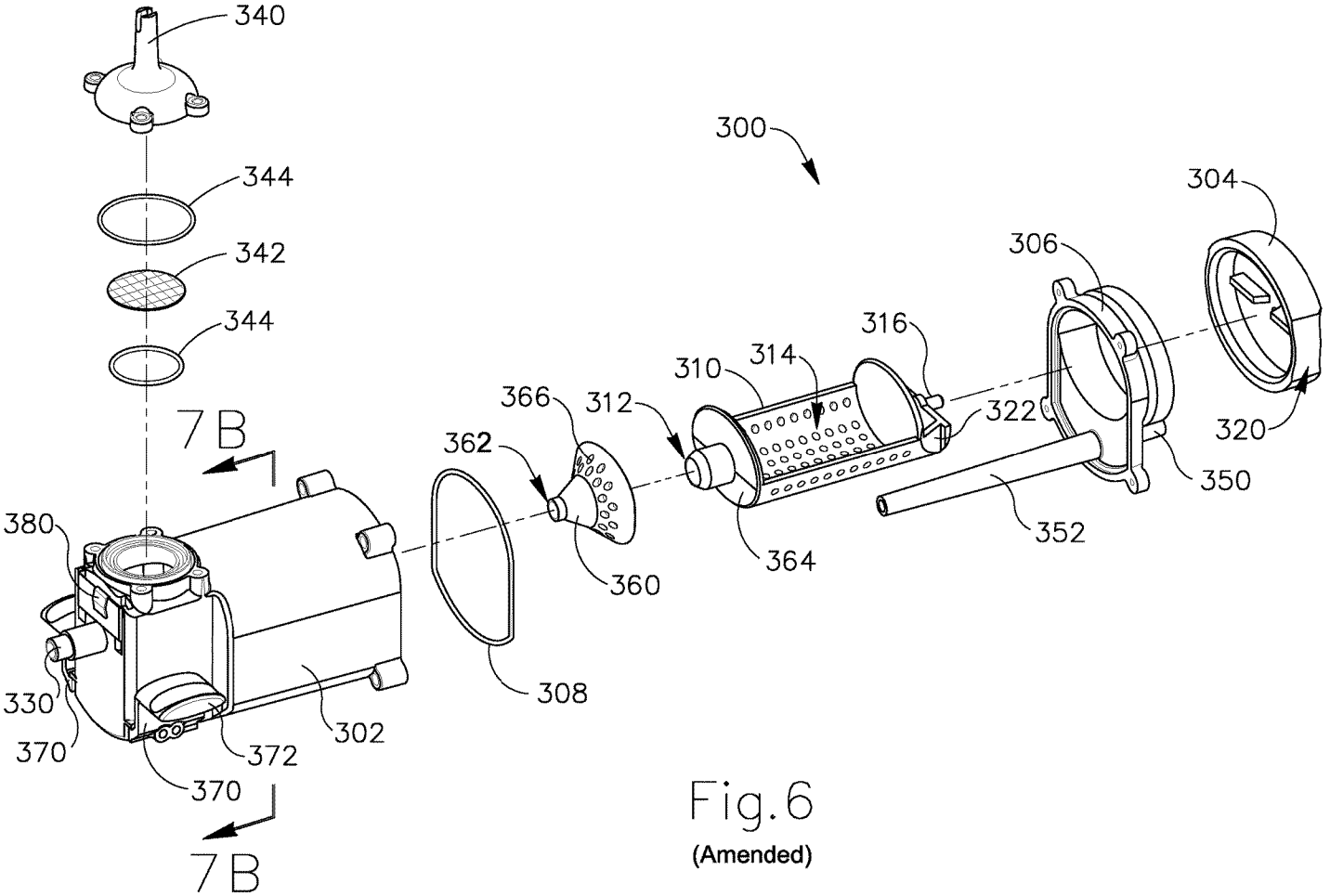
Fig. 6
(Amended)

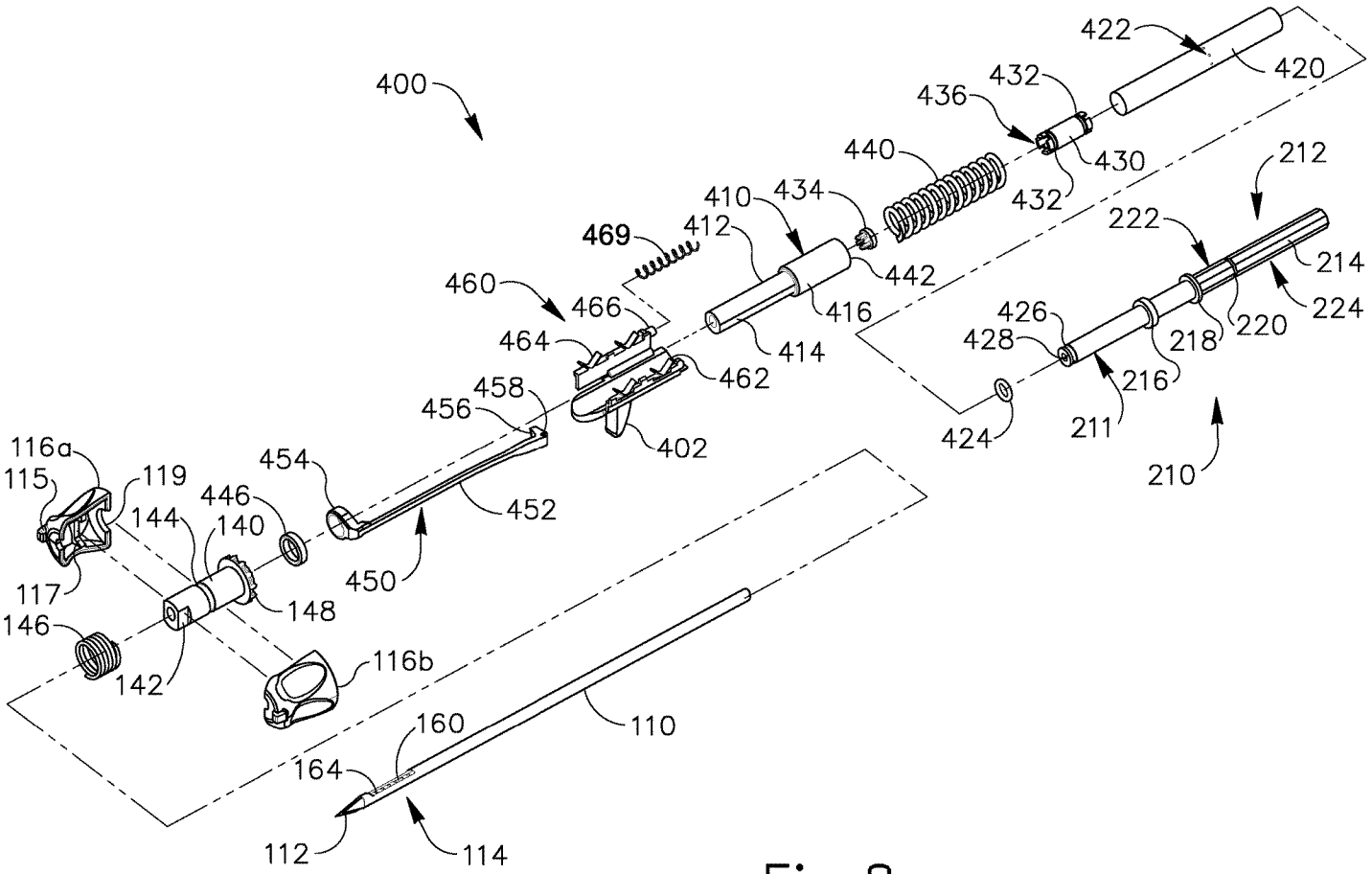
Fig.8
(Amended)

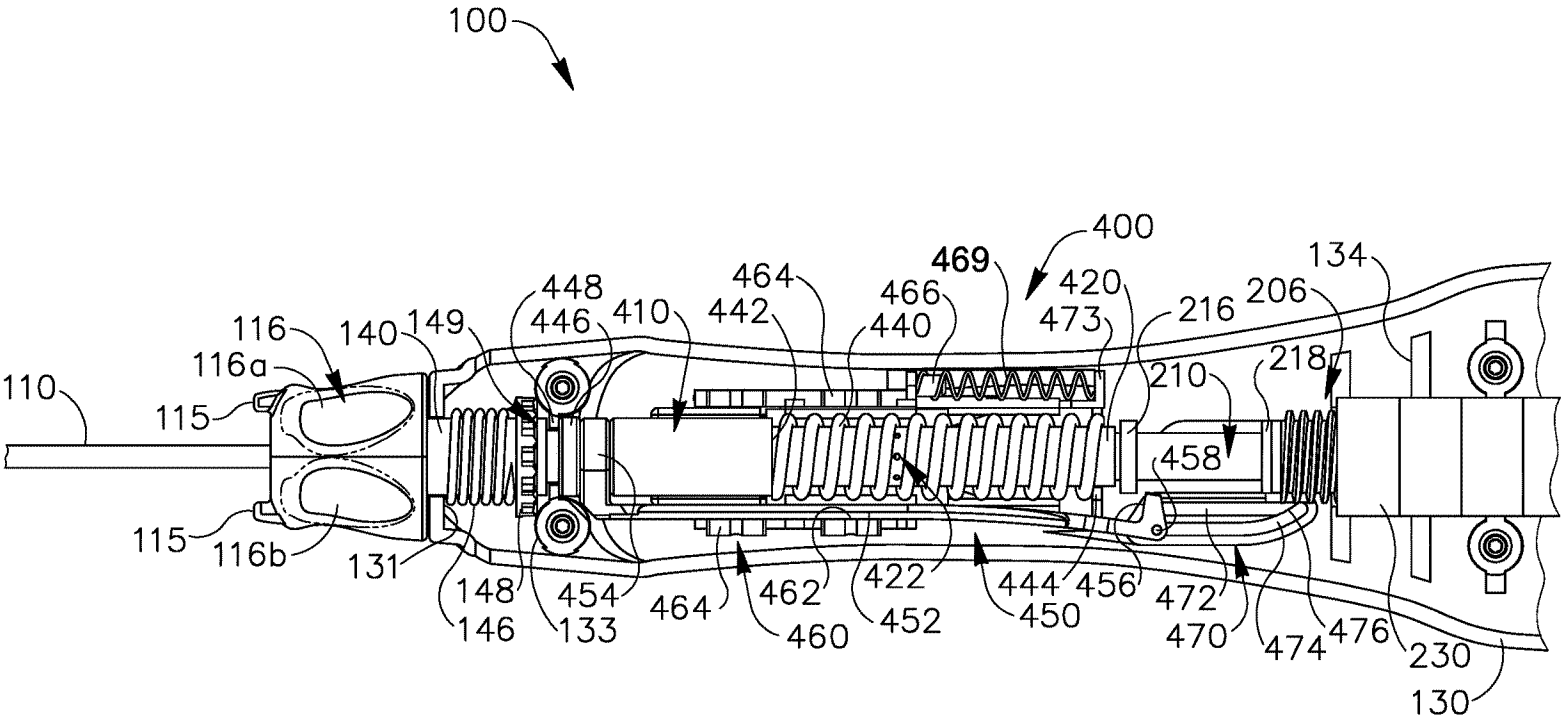
Fig.10A
(Amended)

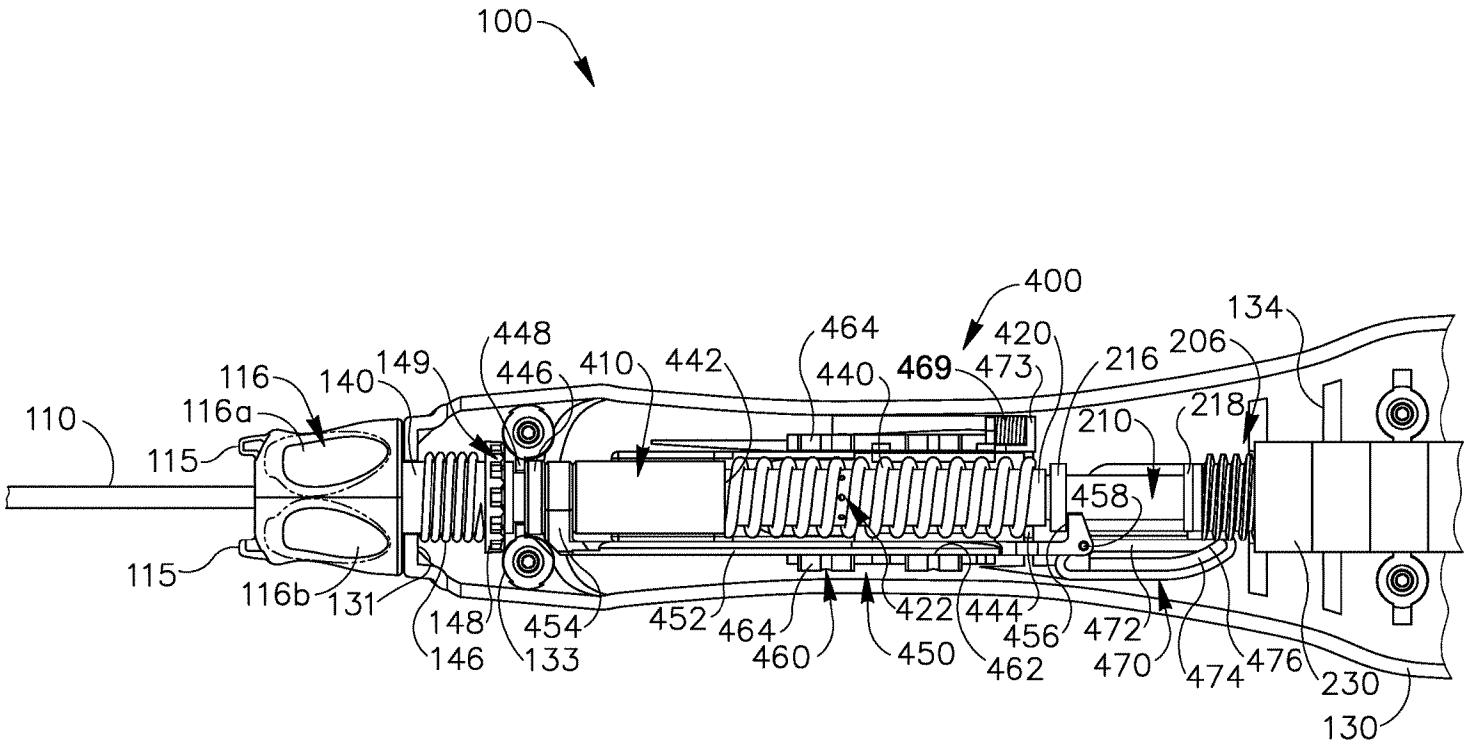
Fig.10B
(Amended)

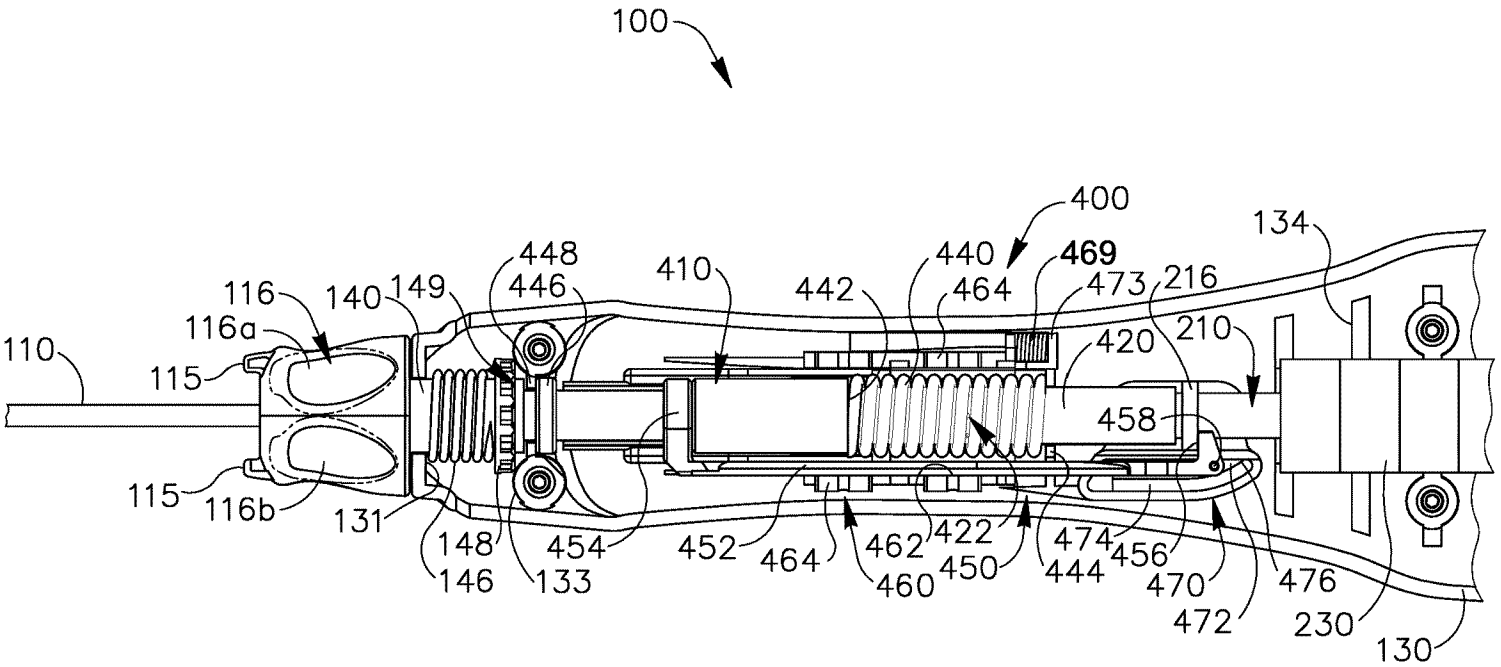
Fig. 10C
(Amended)

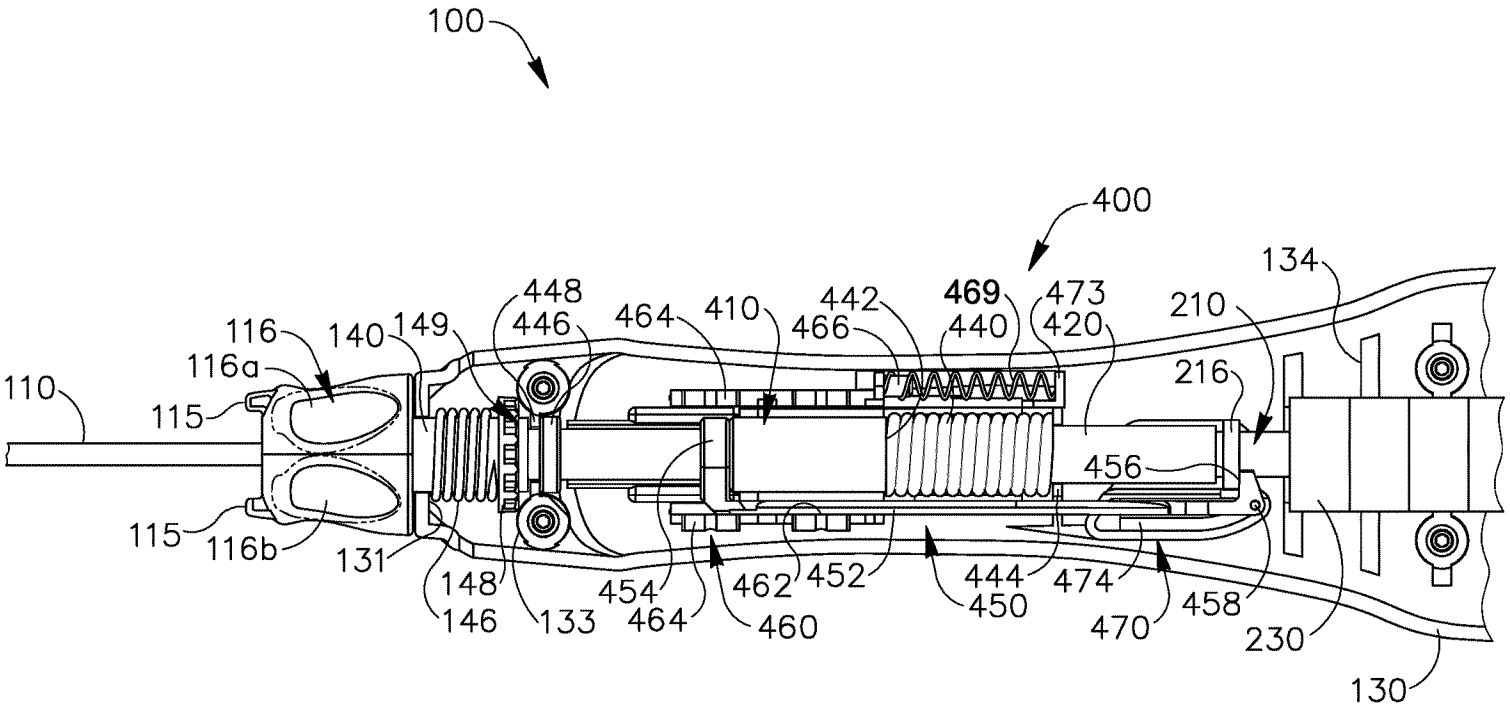
Fig.10D
(Amended)

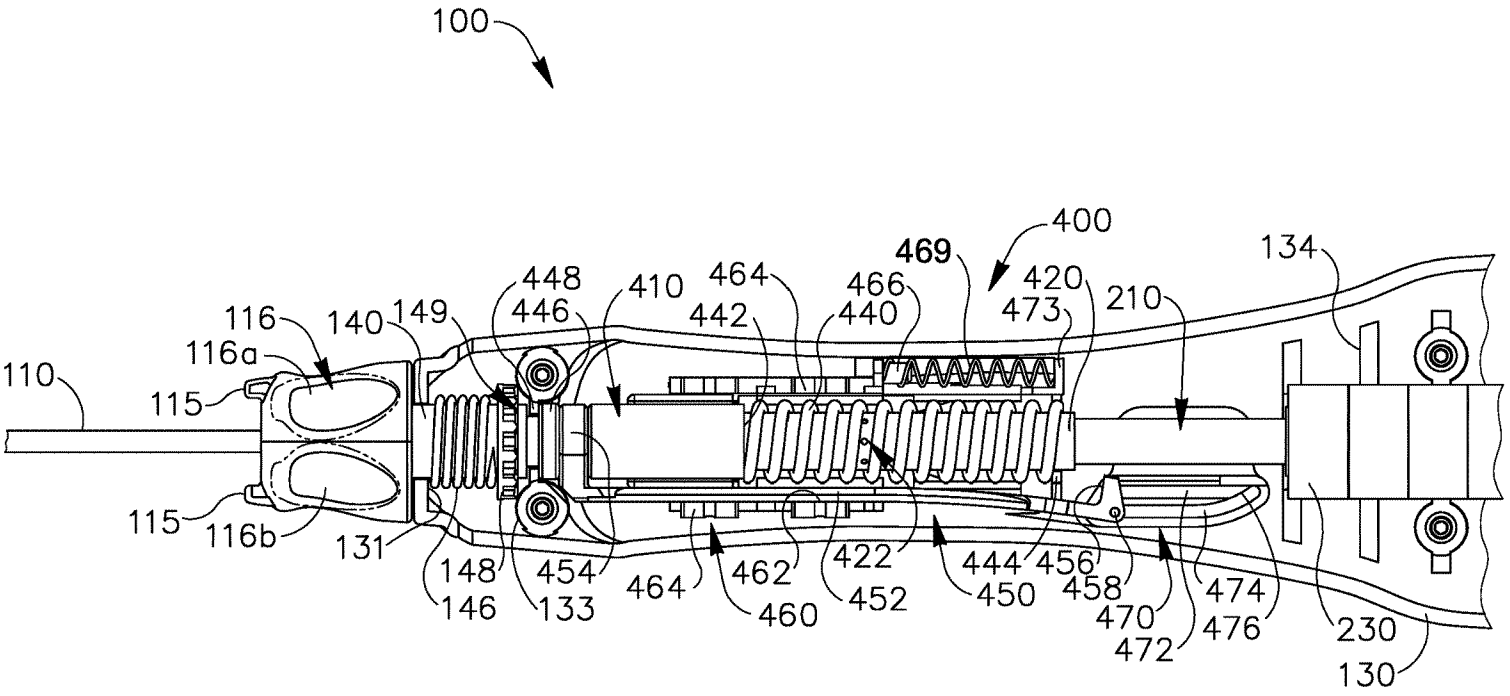
Fig.10E
(Amended)

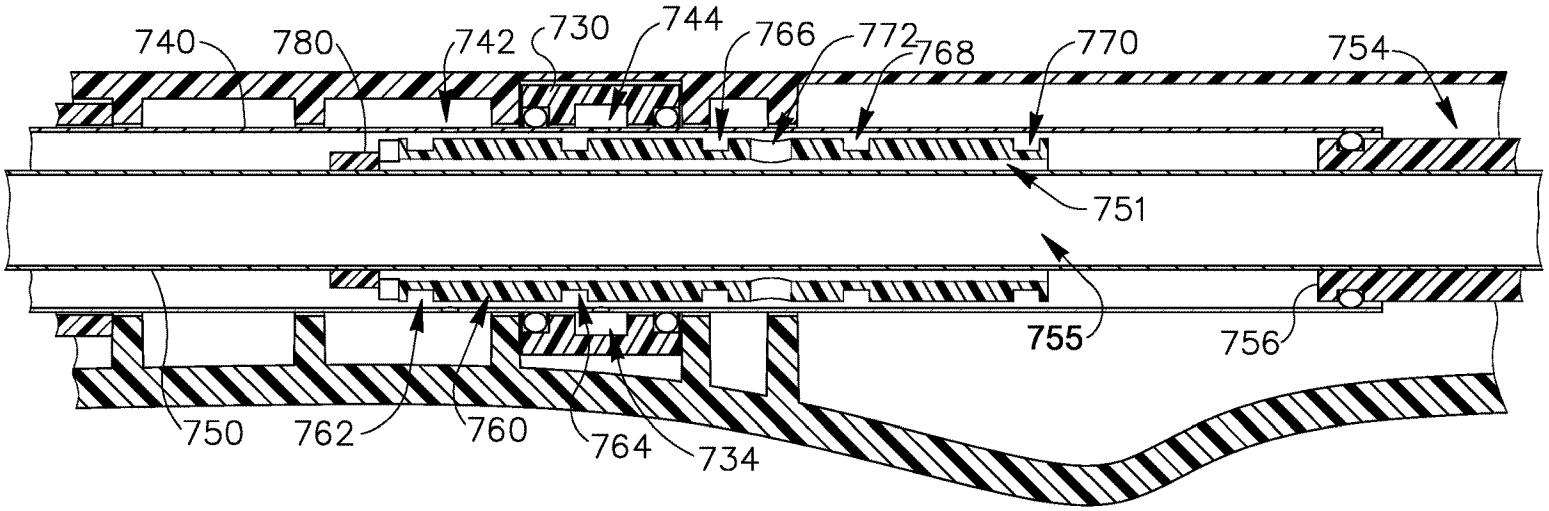
Fig. 18A
(Amended)

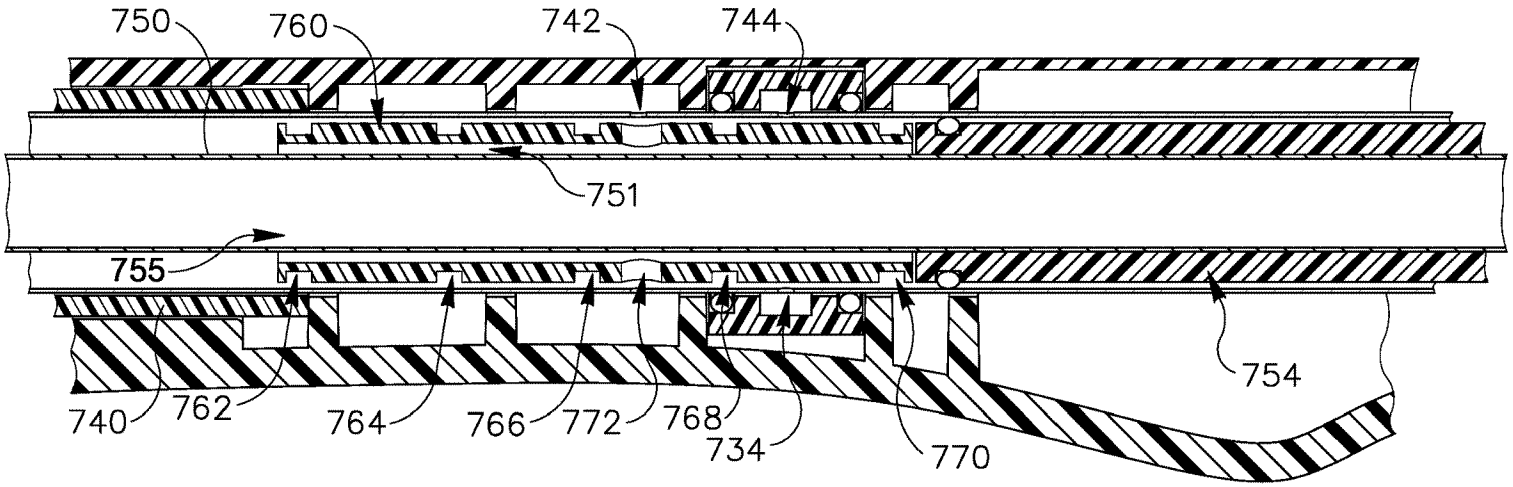
Fig.18B
(Amended)

HANDHELD BIOPSY DEVICE WITH NEEDLE FIRING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

PRIORITY

This application claims priority to U.S. Provisional Application Ser. No. 61/408,795, entitled "Handheld Biopsy Device with Needle Firing," filed Nov. 1, 2010, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Non-Provisional patent application Ser. No. 12/483,305, entitled "Tetherless Biopsy Device with Reusable Portion," filed Jun. 12, 2009; and U.S. Non-Provisional patent application Ser. No. 12/709,624, entitled "Spring Loaded Biopsy Device," filed Feb. 22, 2010. The disclosure of each of the above-cited U.S. patents, U.S. patent application Publications, and U.S. Non-Provisional patent applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 6 depicts an exploded perspective view of tissue sample holder components of the probe of FIG. 3;

FIG. 8 depicts an exploded perspective view of needle firing and valving components of the probe of FIG. 3;

FIG. 10A depicts a partial top plan view of the needle firing components of FIG. 8, with the needle firing mechanism in a ready to arm configuration;

FIG. 10B depicts a partial top plan view of the needle firing components of FIG. 8, with the needle firing mechanism in an armed and ready to retract configuration;

FIG. 10C depicts a partial top plan view of the needle firing components of FIG. 8, with the needle firing mechanism transitioning to a ready to fire configuration;

FIG. 10D depicts a partial top plan view of the needle firing components of FIG. 8, with the needle firing mechanism in a retracted and ready to fire configuration;

FIG. 10E depicts a partial top plan view of the needle firing components of FIG. 8, with the needle firing mechanism in a fired configuration;

FIG. 18A depicts a side cross-sectional view of valving components of the probe in FIG. 15, with a shuttle valve slider in a proximal position;

FIG. 18B depicts a side cross-sectional view of valving components of the probe in FIG. 15, with a shuttle valve slider in a distal position;

Figure 1:
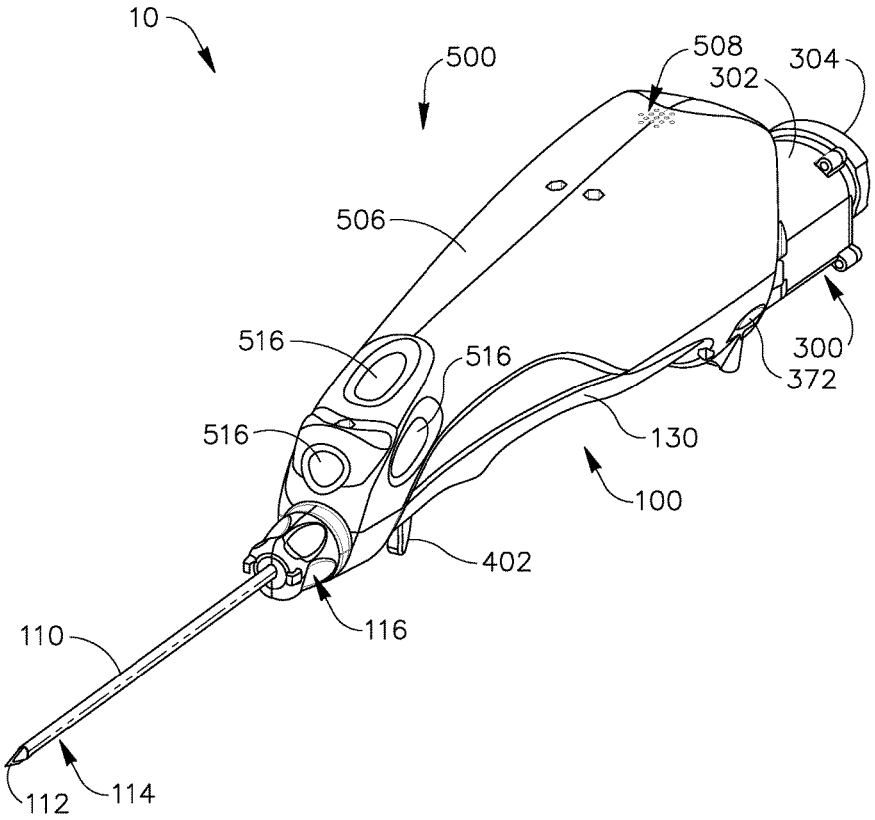
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

Figure 2:
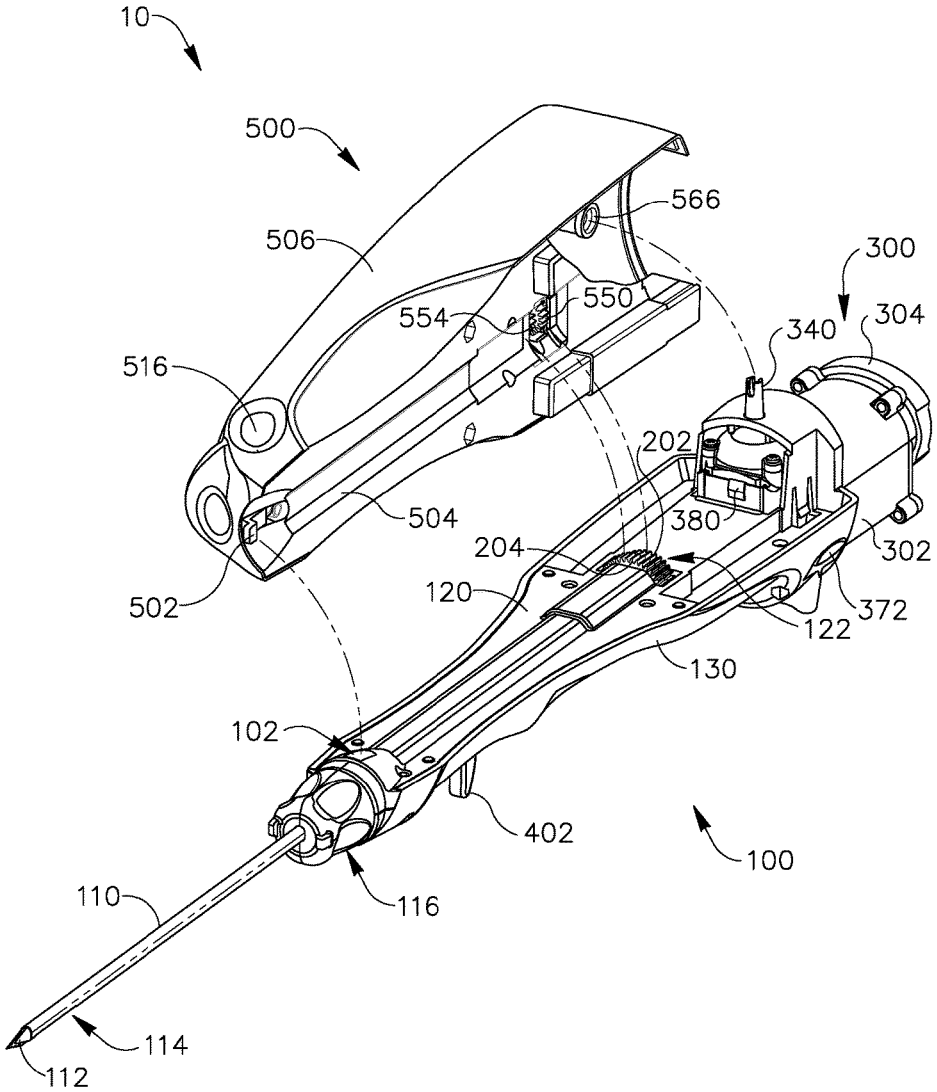
FIG. 2 depicts a perspective view of a probe portion of the biopsy device of FIG. 1 separated from a holster portion of the biopsy device of FIG. 1.
Figure 3:
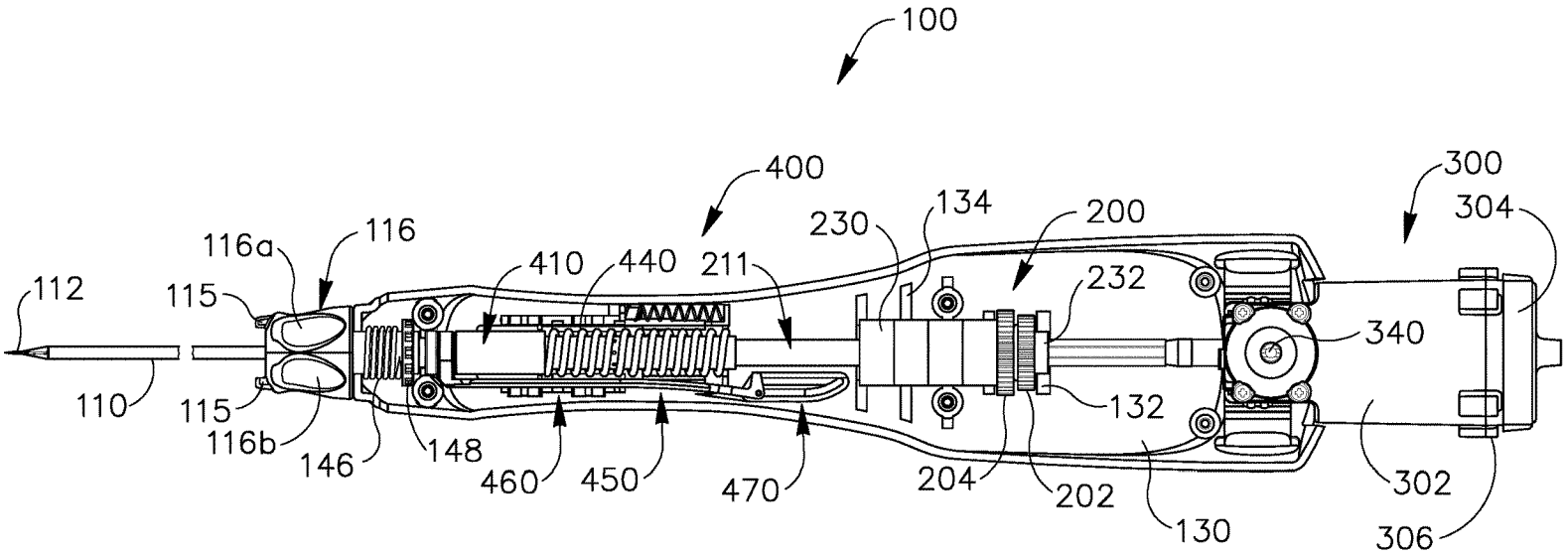
FIG. 3 depicts a top plan view of the probe portion of the biopsy device, with a top chassis removed.
Figure 4:
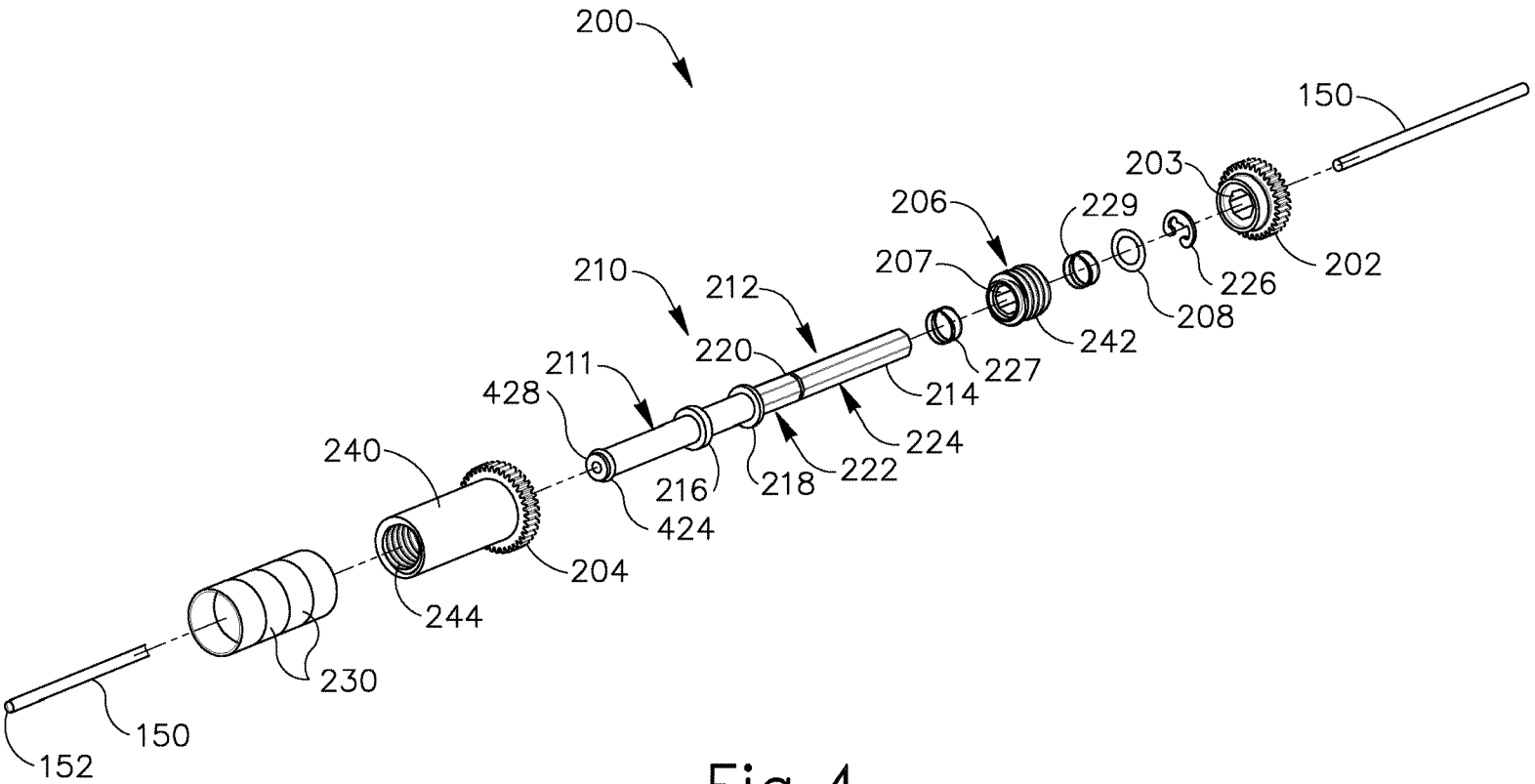
FIG. 4 depicts an exploded perspective view of cutter actuation components of the probe of FIG. 3.

FIGS. 1-2 show an exemplary biopsy device (10). Biopsy device (10) of this example comprises a probe (100) and a holster (500). A needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (500). Indeed, in the present example, and as best seen in FIG. 2, a finger (502) extends distally from holster (500), and is received in a corresponding slot (102) of probe (100) to help secure probe (100) and holster (500) together. Other components of probe (100) and holster (500) mate when probe (100) and holster (500) are coupled together, as will be described in greater detail below. It should be understood that a variety of types of structures, components, features, etc. (e.g., bayonet mounts, latches, clamps, clips, snap fittings, etc.) may be used to provide removable coupling of probe (100) and holster (500). Furthermore, in some biopsy devices (10), probe (100) and holster (500) may be of unitary or integral construction, such that the two components cannot be separated. By way of example only, in versions where probe (100) and holster (500) are provided as separable components, probe (100) may be provided as a disposable component, while holster (500) may be provided as a reusable component. Still other suitable structural and functional relationships between probe (100) and holster (500) will be apparent to those of ordinary skill in the art in view of the teachings herein.

Some variations of biopsy device (10) may include one or more sensors (not shown), in probe (100) and/or in holster (500), that is/are configured to detect when probe (100) is coupled with holster (500). Such sensors or other features may further be configured to permit only certain types of probes (100) and holsters (500) to be coupled together. In addition or in the alternative, such sensors may be configured to disable one or more functions of probes (100) and/or holsters (500) until a suitable probe (100) and holster (500) are coupled together. Of course, such sensors and features may be varied or omitted as desired.

Biopsy device (10) of the present example is sized and configured such that biopsy device (10) may be operated by a single hand of a user. In particular, a user may grasp biopsy device (10), insert needle (100) into a patient's breast, and collect one or a plurality of tissue samples from within the patient's breast, all with just using a single hand. Alternatively, a user may grasp biopsy device (10) with more than one hand and/or with any desired assistance. It should also be understood that biopsy device (10) may be grasped and fully operated by a single hand using a variety of different kinds of grips, including but not limited to a pencil grip. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Probe

FIGS. 3-10 show probe (100) of the present example in greater detail. As noted above, probe (100) includes a distally extending needle (110). Probe (100) also includes a chassis (120) and a base housing (130), which are fixedly secured together. Tissue sample holder (300) is removably coupled with base housing (130) in this example, though it should be understood that tissue sample holder (300) may alternatively be non-removably secured to base housing (130). A pair of gears (202, 204) are exposed through an opening (122) in chassis (120), and are operable to drive a cutter actuation mechanism (200) in probe (100) as will be described in greater detail below. An arming finger grip (402) extends downwardly from the bottom of base housing (130), and is operable to arm a needle firing mechanism (400) in probe (100) as will also be described in greater detail below.

A. Exemplary Needle

Needle (110) of the present example includes a piercing tip (112), a lateral aperture (114) located proximal to tip (112), and a rotation knob (116). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. Tip (112) may also be configured to provide greater echogenicity than other portions of needle (110), providing enhanced visibility of tip (112) under ultrasound imaging. By way of example only, tip (112) may be configured in accordance with any of the teachings in U.S. Non-Provisional patent application Ser. No. 12/875,200, entitled "Echogenic Needle for Biopsy Device," filed Sep. 3, 2010, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A tubular cutter (150) having a sharp distal edge (152) is located within needle (110). As described in greater detail below, cutter (150) is operable to rotate and translate relative to needle (110) and past lateral aperture (114) to sever a tissue sample from tissue protruding through lateral aperture (114). While lateral aperture (114) is shown oriented in a downward position in FIG. 1, it should be understood that needle (110) may be rotated to orient lateral aperture (114) at any desired angular position about the longitudinal axis of needle (110). Such rotation of needle (110) is facilitated in the present example by rotation knob (116), which is secured to needle (110). In particular, and now referring to FIG. 8, a needle overmold (410) is fixedly secured to needle (110), and is configured to transfer rotation from rotation knob (116) to needle (110). By way of example only, needle (110) may be formed of metal, and needle overmold (410) may be formed of a plastic material that is overmolded about needle (110) to unitarily secure and form needle overmold (410) to needle (110). Needle overmold (410) and needle (110) may alternatively be formed of any other suitable material(s), and may be secured together in any other suitable fashion. Needle overmold (410) includes a distal portion (412) having a pair of flats (414). Distal portion (412) of needle overmold (410) is slidably disposed in a bore (not shown) of a rotation hub (140). This bore of rotation hub (140) includes flats that complement flats (414) of needle overmold (410), such that rotation of rotation hub (140) will rotate needle overmold (140), thereby rotating needle (110). The relationship between rotation hub (140) and needle overmold (410) in the present example will nevertheless permit needle (110) and needle overmold (410) to unitarily translate relative to rotation hub (140), as will be described in greater detail below.

Rotation hub (140) also includes a pair of flats (142) and an annular recess (144). As shown in FIG. 9, rotation knob (116) of the present example is formed of a first half (116a), and a second half (116b), which are configured to snap fit together about rotation hub (140). Halves (116a, 116b) have bosses (117) that engage flats (142) of rotation hub (140), such that rotation of rotation knob (116) will rotate rotation hub (140). Halves (116a, 116b) also include proximal rims (119) that engage annular recess (144) of rotation hub (140), such that rotation knob (116) will translate longitudinally with rotation hub (140). Rotation knob (116) of the present example also includes a pair of distal latching members (115), which may removably engage other components of a biopsy system such as a targeting set for use in an MRI biopsy setting, etc.

As best seen in FIGS. 10A-10E, rotation hub (140) also includes a proximal flange (148) having a plurality of notches (149) formed therein. A coil spring (146) is coaxially disposed about rotation hub (140), and is positioned between a proximally facing distal inner surface (131) of base housing (130) and the distal face of proximal flange (148) of rotation hub (140). Spring (146) is resiliently biased to urge proximal flange (148) proximally toward posts (133) of base housing (130). A boss (not shown) extends upwardly from the lower surface of base housing (130) and is configured to engage a downwardly presented notch (149) of proximal flange (148). Such engagement substantially secures the rotational position of rotation hub (140) about the longitudinal axis defined by needle (110). The bias of spring (146) further promotes engagement between this boss and whichever notch (149) is downwardly presented by urging proximal flange (148) proximally. Thus, in order to change the rotational orientation of needle (110), a user may grasp rotation knob (116) and push or pull rotation knob (116) distally against the resilient bias of spring (146) to disengage the boss from the most downwardly presented notch (149), rotate rotation knob (116) while holding rotation knob (116) in a distal position to rotate needle (110) (thereby re-orienting lateral aperture (114) about the longitudinal axis of needle (110)), then release rotation knob (116) to allow spring (146) to move rotation hub (140) proximally (thereby engaging the boss with the notch (149) now downwardly presented). With needle (110) at the adjusted angular orientation, the engagement between the boss and the now downwardly presented notch (149), promoted by the resilient bias of spring (146), will maintain needle (110) at the adjusted angular orientation. In some versions, the underside of chassis (120) includes a downwardly extending boss that engages an upwardly presented notch (149), in addition to or in lieu of an upwardly extending boss of base housing (130) engaging a downwardly presented notch (149).

Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As best seen in FIGS. 8 and 5A-5C, needle (110) also includes a longitudinal wall (160) extending proximally from the proximal portion of tip (112). While wall (160) does not extend along the full length of needle (110) in this example, it should be understood that wall (160) may extend the full length of needle (110) if desired. Wall (160) of the present example proximally terminates at a longitudinal position that is just proximal to the longitudinal position of distal cutting edge (152) of cutter (150) when cutter (150) is in a proximal position (see FIG. 5C). Thus, wall (160) and cutter (150) together define a second lumen (162) that is lateral to and parallel to cutter (150). Of course, wall (160) may alternatively proximally terminate at a longitudinal position that is just distal to the longitudinal position of distal cutting edge (152) of cutter (150) when cutter (150) is in a proximal position; or wall (160) may terminate at any other suitable longitudinal position. Wall (160) includes a plurality of openings (164) that provide fluid communication between second lumen (162) and the upper portion of needle (110), as well as fluid communication between second lumen (162) and the lumen (154) of cutter (150). For instance, as will be described in greater detail below, second lumen (162) may selectively provide atmospheric air to vent cutter lumen (154) during operation of biopsy device (10) as will be described in greater detail below. Openings (164) are arranged such that at least one opening (164) is located at a longitudinal position that is distal to the distal edge of lateral aperture (114). Thus, cutter lumen (154) and second lumen (162) may remain in fluid communication even when cutter (150) is advanced to a position where cutting edge (152) is located at a longitudinal position that is distal to the longitudinal position of the distal edge of lateral aperture (114) (se FIG. 5A). Of course, as with any other component described herein, any other suitable configurations may be used.

It should be understood that, as with other components described herein, needle (110) may be varied, modified, substituted, or supplemented in a variety of ways; and that needle (110) may have a variety of alternative features, components, configurations, and functionalities. A plurality of external openings (not shown) may also be formed in needle (110), and may be in fluid communication with second lumen (162). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Cutter (150) may also include one or more side openings (not shown). Of course, as with other components described herein, such external openings in needle (110) and cutter (150) are merely optional. As another merely illustrative example, needle (110) may simply lack second lumen (162) altogether in some versions. Other suitable alternative versions, features, components, configurations, and functionalities of needle (110) will be apparent to those of ordinary skill in the art in view of the teachings herein.

B. Exemplary Cutter Actuation Mechanism

As shown in FIGS. 3-5C, cutter actuation mechanism (200) of the present example comprises a variety of components that interact to provide simultaneous rotation and distal translation of cutter (150) relative to base housing (130) and needle (110) in a firing stroke. Cutter actuation mechanism (200) is also operable to retract cutter (150) proximally to ready cutter (150) for firing. Cutter actuation mechanism (200) of the present example includes a pair of gears (202, 204), a lead screw (206), a cutter sleeve or overmold (210), and a plurality of sleeves (230). All of these components (202, 204, 206, 210, 230) are coaxially aligned with cutter (150). Cutter overmold (210) is fixedly secured to cutter (150), such that cutter overmold (210) and cutter (150) will rotate and translate unitarily together in the present example. By way of example only, cutter (150) may be formed of metal, and cutter overmold (210) may be formed of a plastic material that is overmolded about cutter (150) to unitarily secure and form cutter overmold (210) to cutter (150). Cutter overmold (210) and cutter (150) may alternatively be formed of any other suitable material(s), and may be secured together in any other suitable fashion. Cutter overmold (210) includes a proximal portion (212) having external flats (214), a distal flange (216), and a proximal flange (218).

An annular recess (220) divides proximal portion (212) of cutter overmold (210) into a distal region (222) and a proximal region (224). Lead screw (206) is slidably positioned along distal region (222) of proximal portion (212). A clip (226) is secured to annular recess (220), such that lead screw (206) is retained between clip (226) and proximal flange (218). Lead screw (206) includes internal flats (207) that complement external flats (214) of cutter overmold (210). In particular, engagement between flats (207, 214) provides simultaneous rotation of lead screw (206) and cutter overmold (210) while also permitting lead screw (206) to translate relative to cutter overmold (210). Such translation will be restricted by clip (226) and proximal flange (218). Furthermore, a pair of coil springs (227, 229) are configured to resiliently bear against opposite ends of lead screw (206). A washer (208) is located between proximal spring (229) and clip (226) in this example, though it should be understood that washer (208) may be omitted if desired. The spacing between flange (218) and washer (208) permits some freedom of movement for lead screw (206) along part of distal region (222) between flange (218) and washer (208); while springs (227, 229) bias lead screw (206) to be substantially centered between flange (218) and washer (208). It should be understood that any other suitable type of resilient member may be used in addition to or in lieu of coil springs (227, 229). It should also be understood that the location of lead screw (206) between flange (218) and washer (208) may be substantially fixed, if desired.

Gear (202) also includes internal flats (203) that complement external flats (214) of cutter overmold (210). In particular, engagement between flats (203, 214) provides simultaneous rotation of gear (202) and cutter overmold (210) while also permitting lead cutter overmold (210) translate relative to gear (202). While all flats (203, 207, 214) are octagonal in the present example, it should be understood that other suitable structures may be used, including but not limited to hexagonal flats, complementary keys and keyways, etc. The longitudinal position of gear (202) remains substantially constant relative to base housing (130) during operation of biopsy device (10) of the present example. As shown in FIGS. 3 and 5A-5C, gear (202) is supported by a bushing (232), which is disposed within an integral support structure (132) of base housing (130). Gear (202) is positioned and configured to mesh with a complementary gear (550) of holster (500) when probe (100) and holster (500) are coupled together. As will be described in greater detail below, components in holster (500) are operable to rotatingly drive gear (550), which in turn rotates gear (202). As noted above and as will also be described in greater detail below, rotation of gear (202) provides rotation of cutter overmold (210), cutter (150), and lead screw (206), which further provides translation of cutter (150).

A threaded sleeve (240) extends distally from gear (204). Threaded sleeve (240) and gear (204) rotate unitarily in the present example. For instance, threaded sleeve (240) and gear (204) may be molded as a single unitary piece, as two separate pieces that are later joined together, etc. As shown in FIG. 5B, cutter actuation mechanism (200) is configured such that external threading (242) of lead screw (206) meshes with internal threading (244) of threaded sleeve (240). This meshing of threading (242, 244) provides translation of lead screw (206), and hence, cutter overmold (210) and cutter (150), when lead screw (206) and threaded sleeve (240) are rotated relative to each other. The longitudinal position of gear (204) and threaded sleeve (240) remains substantially constant relative to base housing (130) during operation of biopsy device (10) of the present example. As shown in FIGS. 3 and 5A-5C, threaded sleeve (240) is supported by sleeves (230), which are disposed within integral support structures (134) of base housing (130) and chassis (120). Gear (204) is positioned and configured to mesh with a complementary gear (554) of holster (500) when probe (100) and holster (500) are coupled together. As will be described in greater detail below, components in holster (500) are operable to rotatingly drive gear (554), which in turn rotates gear (204). While sleeves (230) are shown as separate components, it should be understood that a single sleeve (230) may be used.

As described in greater detail below, holster (500) may be activated to rotate gears (550, 554) simultaneously. As noted above, gears (202, 204) mesh with gears (550, 554) when probe (100) and holster (500) are coupled together, such that simultaneous rotation of gears (550, 554) provides corresponding simultaneous rotation of gears (202, 204). This further provides corresponding simultaneous rotation of cutter overmold (210), cutter (150), lead screw (206), and sleeve (240). It should also be understood that gears (550, 554) have different pitch diameters in the present example (i.e., the pitch diameter of gear (550) is different from the pitch diameter of gear (554)). Gears (202, 204) also have different pitch diameters (i.e., the pitch diameter of gear (202) is different from the pitch diameter of gear (204)). Accordingly, when a motor (528) in holster (500) that drives gears (550, 554) rotates at one rotational speed, gear (202) and threaded sleeve (240) simultaneously rotate in the same direction as each other yet at different rotational speeds relative to each other. Since rotation of lead screw (206) is driven by rotation of gear (202), lead screw (206) and threaded sleeve (240) also simultaneously rotate in the same direction as each other yet at different rotational speeds relative to each other.

Even though lead screw (206) and threaded sleeve (240) rotate simultaneously in the same direction, the difference between rotational speeds of lead screw (206) and threaded sleeve (240) provide a net result of lead screw (206) rotating relative to threaded sleeve (240), and such relative rotation provides translation of cutter (150) as cutter (150) rotates. By way of example only, with motor (528) in holster (500) providing an output speed of approximately 8,000 rpm, the above-described configuration may provide rotation of cutter (150) at a speed of approximately 1,000 rpm and rotation of threaded sleeve (240) at a speed of approximately 850 rpm, resulting in a net rotation of cutter (150) relative to threaded sleeve (240) at approximately 150 rpm. Of course, any other suitable differential may be provided. In the present example, the direction of rotation provided by motor (528) is simply reversed to reverse the direction of translation of cutter (150). Alternatively, cutter actuation mechanism (200) may be configured to be self-reversing, such that cutter (150) may be translated distally and proximally without reversing the direction of motor (528) rotation. By way of example only, cutter actuation mechanism (200) may be configured to self-reverse in accordance with the teachings of U.S. Pub. No. 2010/0292607, entitled "Tetherless Biopsy Device with Self-Reversing Cutter Drive Mechanism," published Nov. 18, 2010, the disclosure of which is incorporated by reference herein.

Figure 5A:
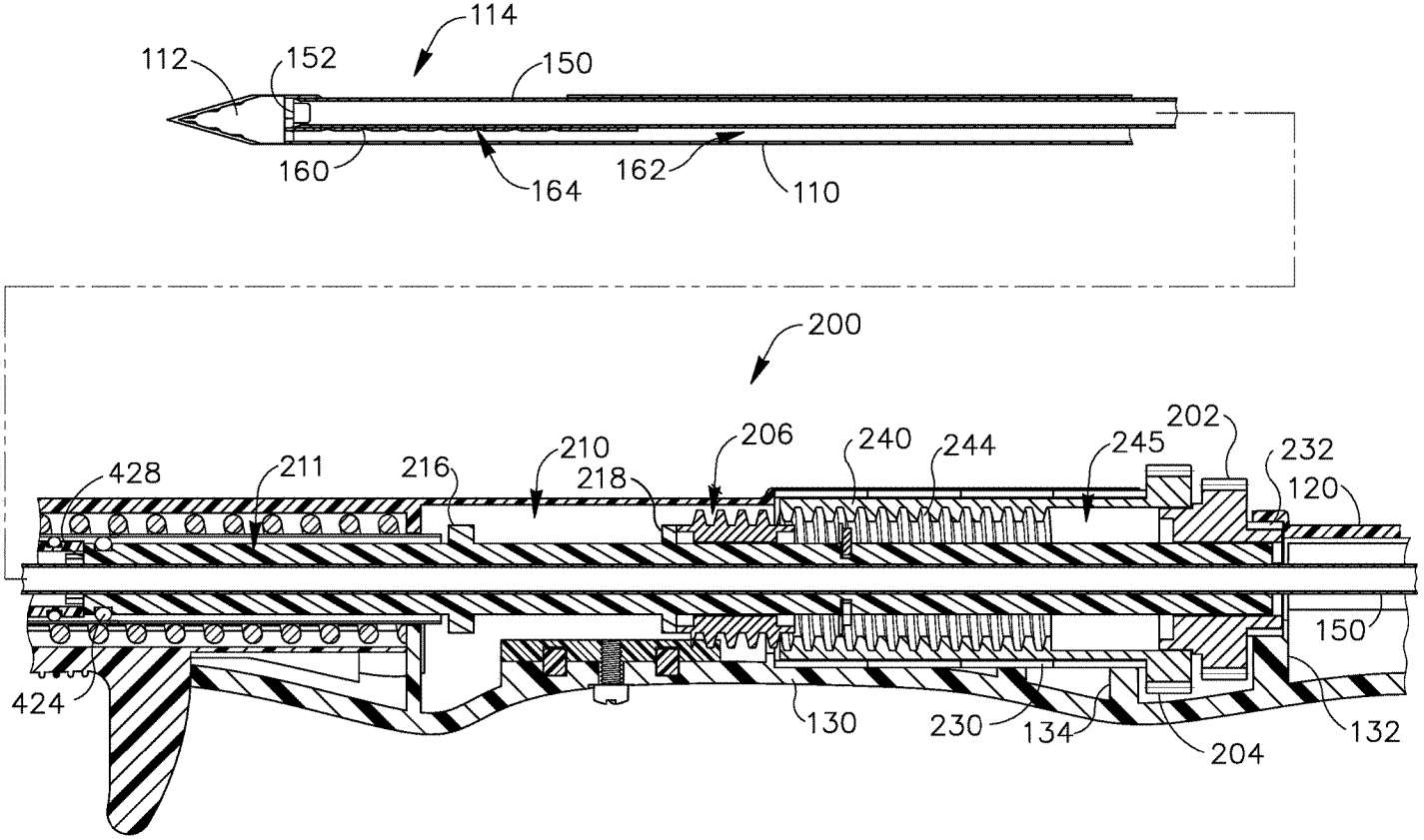
FIG. 5A depicts a partial cross-sectional side view of the cutter actuation components of FIG. 4, as well as a distal portion of the needle and cutter, with the cutter in a distal position.
Figure 5B:
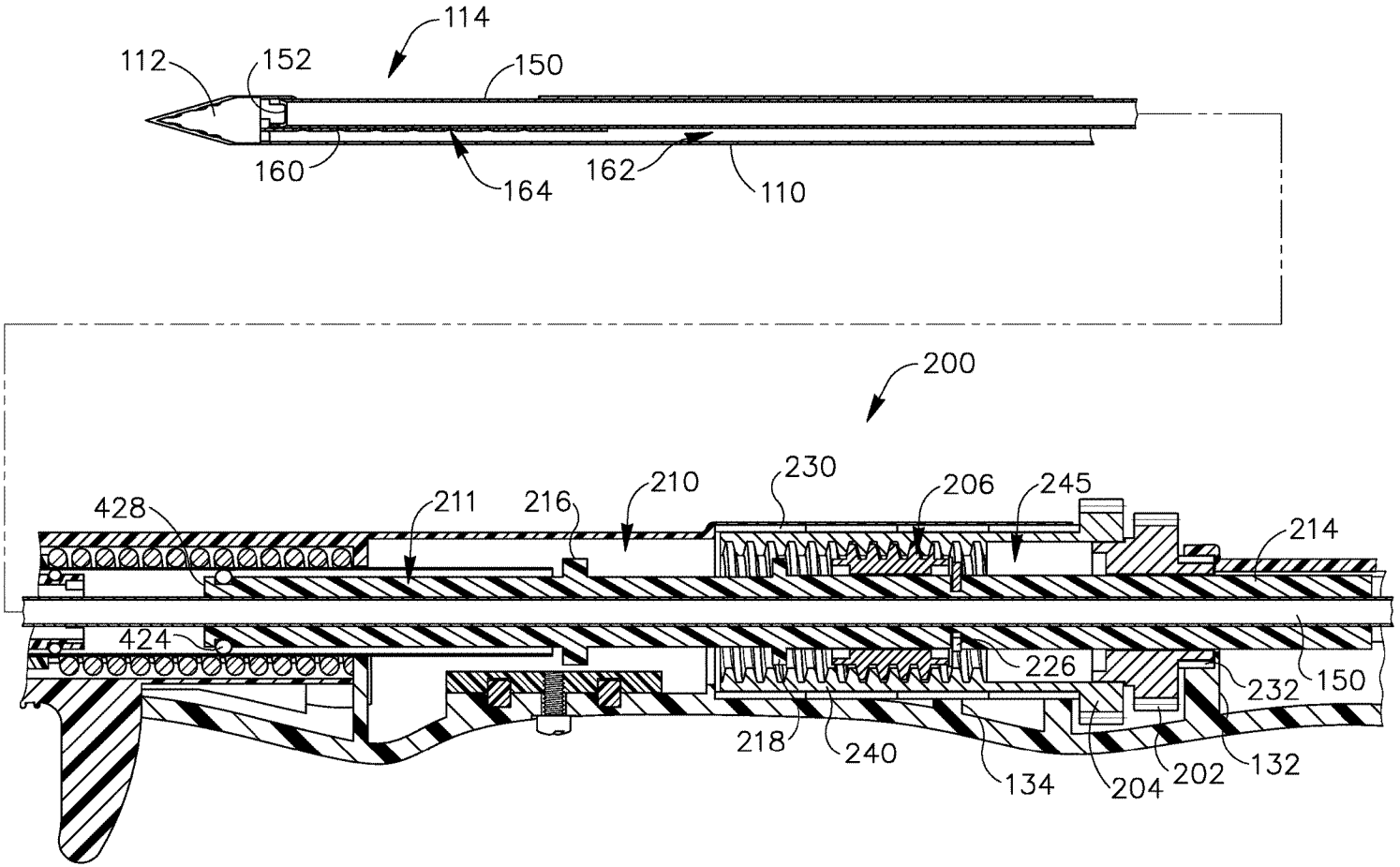
FIG. 5B depicts a partial cross-sectional side view of the cutter actuation components of FIG. 4, as well as a distal portion of the needle and cutter, with the cutter in an intermediate position.

In one merely illustrative example of operation of cutter actuation mechanism (200), cutter (150) may be initially located in a distal-most position, such that lateral aperture [(14)] (*114*) is "closed" as shown in FIG. 5A; with lead screw (206) being positioned distal to threaded sleeve (240), as also shown in FIG. 5A. Spring (227) biases lead screw (206) proximally to engage threading (242) with threading (244). At this stage, rotation of cutter (150) relative to threaded sleeve (240) in a first rotational direction will not result in any distal translation of cutter (150) (e.g., lead screw (206) will essentially "freewheel"); while rotation of cutter (150) relative to threaded sleeve (240) in a second rotational direction will result in proximal translation of cutter (150). As cutter (150) is rotated by motor (528) and cutter actuation mechanism (200) in the second rotational direction, cutter actuation mechanism (200) causes cutter (150) to retract proximally, as shown in FIG. 5B. As noted above, such proximal or rearward translation may be effected through engagement of threading (242, 244), and due to lead screw (206) rotating at a faster speed than threaded sleeve (240). Lead screw (206) continues to traverse threading (244) of threaded sleeve (240) as cutter (150) continues to retract proximally.

Figure 5C:
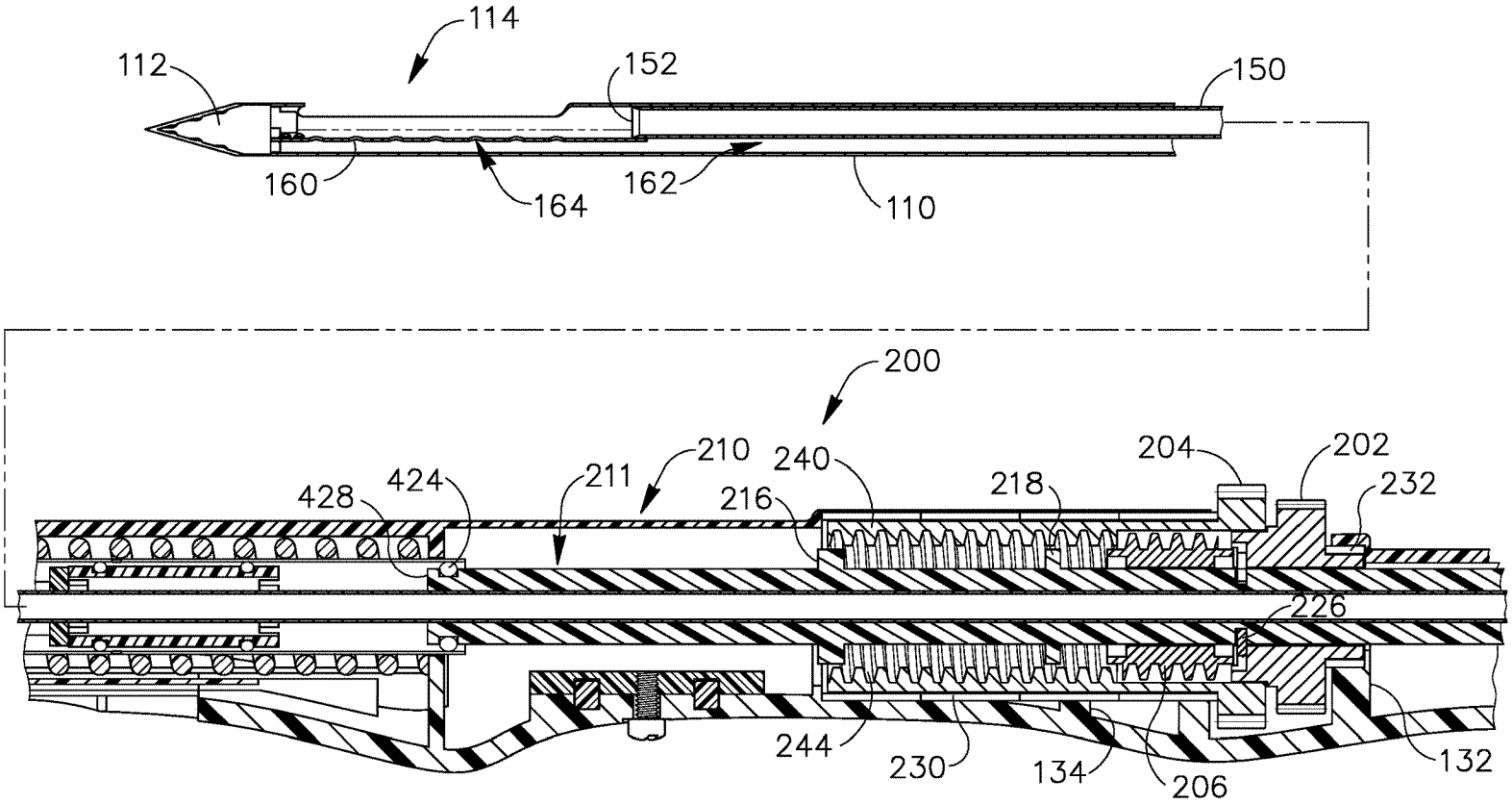
FIG. 5C depicts a partial cross-sectional side view of the cutter actuation components of FIG. 4, as well as a distal portion of the needle and cutter, with the cutter in a proximal position.

Cutter (150) then reaches a proximal-most position, such that lateral aperture (114) is "opened" as shown in FIG. 5C. At this stage, lead screw (206) is positioned at a proximal smooth interior section (245) of threaded sleeve (240) that lacks threading (244), as also shown in FIG. 5C. Spring (229) biases lead screw (206) distally to engage threading (242) with threads (244). At this stage, continued rotation of cutter (150) relative to threaded sleeve (240) in the second rotational direction will not result in any further proximal translation of cutter (150) (e.g., lead screw (206) will essentially "free-wheel"); while rotation of cutter (150) relative to threaded sleeve (240) in the second rotational direction will result in distal translation of cutter (150). To that end, motor (528) may again be activated, with its rotation direction being reversed to reverse the rotation direction of cutter (150) and associated components. Such reversed rotation of cutter (150) causes cutter (150) to advance distally to reach the distal-most position again, as shown in FIG. 5A.

When cutter (150) is retracted to a proximal position, thereby effectively opening lateral aperture (114), tissue may prolapse through lateral aperture (114) under the force of gravity, due to internal pressure of the tissue (e.g., caused by displacement of the tissue upon insertion of needle (110), etc.), caused by manual external palpation of the patient's breast by the physician, and/or under the influence of vacuum provided through cutter lumen (154) as described elsewhere herein. When cutter (150) is then advanced distally, distal edge (152) severs tissue protruding through lateral aperture (114). This severed tissue is captured within cutter lumen (154). A vacuum applied through cutter lumen (154) (as described herein or otherwise) will be encountered by the proximal face of a severed tissue sample within cutter lumen (154). A vent may be applied through second lumen (162) of needle (110), which may be communicated to the distal face of the severed tissue sample via openings (164), providing a pressure differential for the severed tissue sample. This pressure differential may facilitate proximal transport of the severed tissue sample through cutter lumen (154), whereby the severed tissue sample eventually reaches tissue sample holder (300) as described elsewhere herein. Alternatively, tissue samples severed by cutter (150) may be communicated proximally to tissue sample holder (300) or be otherwise dealt with in any other suitable fashion.

Of course, any other suitable structures, components, configurations, or techniques may be used to provide translation and/or rotation of cutter (150). It should therefore be understood that, as with other components described herein, cutter actuation mechanism (200) may be varied, modified, substituted, or supplemented in a variety of ways; and that cutter actuation mechanism (200) may have a variety of alternative features, components, configurations, and functionalities. By way of example only, biopsy device (10) may be configured such that cutter (150) does not translate (e.g., such that cutter (150) merely rotates, etc.); or such that cutter (150) does not rotate (e.g., such that cutter (150) merely translates, etc.). As another merely illustrative example, cutter (150) may be actuated pneumatically in addition to or in lieu of being actuated by mechanical components. Other suitable alternative versions, features, components, configurations, and functionalities of cutter actuation mechanism (200) will be apparent to those of ordinary skill in the art in view of the teachings herein.

C. Exemplary Tissue Sample Holder

As shown in FIGS. 6-7, tissue sample holder (300) of the present example comprises an outer cup (302) and a cap (304), with a frame (306) interposed between cap (304) and cup (302). A seal (308) is interposed between frame (306) and cup (302). Tissue sample holder (300) also includes a collection tray (310). Collection tray (310) is configured to receive and hold tissue samples that are captured by cutter (150) and that are communicated proximally through cutter (150) as will be described in greater detail below. A distal port (312) of collection tray (310) aligns with the longitudinal axis of cutter (150) such that severed tissue samples communicated proximally through cutter lumen (154) will be received on collection tray (310) via distal port (312). Collection tray (310) includes a plurality of openings (314) that are sized and configured to allow fluids to drain through collection tray (310) while also retaining tissue samples on collection tray (310). In some versions, outer cup (302) is transparent and/or translucent, allowing a user of biopsy device (10) to see tissue samples residing on collection tray (310). Of course, outer cup (302) may alternatively be opaque or any desired combination of transparent, translucent, and/or opaque.

A protrusion (316) protrudes proximally from collection tray (310), and is removably received in an opening (318) formed in cap (304). Cap (304) is formed of an elastomeric material, such that friction substantially secures collection tray (310) to cap (304). However, collection tray (310) may be decoupled from cap (304) by first withdrawing cap (304) and collection tray (310) together from cup (302), then squeezing side portions (320) of cap (304) inwardly toward each other. For instance, portions of cap (304) may bear against ramped surfaces (322) of collection tray (310) when side portions (320) of cap (304) are squeezed inwardly toward each other, urging collection tray (310) distally away from cap (304). Thus, in some versions, cap (304) and collection tray (310) may be together removed from cup (302), with tissue samples residing on collection tray (310), then collection tray (310) may be ejected from cap (304) by squeezing side portions (320) inwardly toward each other and then releasing to deposit collection tray and the tissue samples directly into a cup of formalin (not shown), etc. These features of tissue sample holder (300) (among other features of tissue sample holder (300)) may thus be configured an operable in accordance with the teachings of U.S. Provisional Patent App. No. 61/381,466, entitled "Biopsy Device Tissue Sample Holder with Removable Basket," filed Sep. 10, 2010, the disclosure of which is incorporated by reference herein. It should also be understood that the elastomeric properties of cap (304) may provide a substantially fluid tight seal with frame (306). In addition, the elastomeric properties of cap (304) provide a substantially fluid tight seal against protrusion (316) when protrusion (316) is inserted in opening (318). Of course, collection tray (310) and cap (304) may have any other suitable components, features, configurations, and relationships.

Figure 7A:
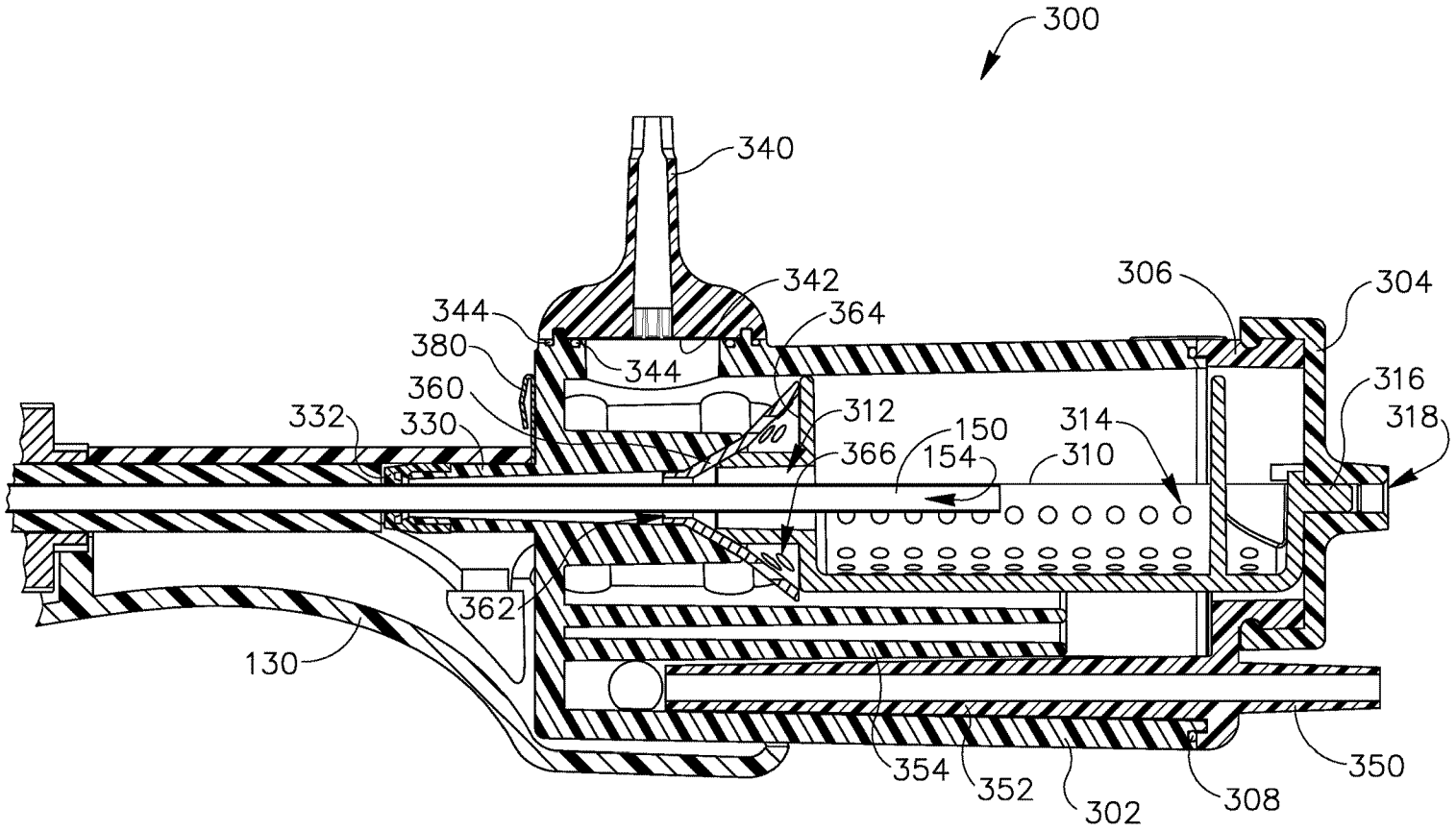
FIG. 7A depicts a partial cross-sectional side view of the tissue sample holder of FIG. 6.

The hollow interior of outer cup (302) is in fluid communication with cutter lumen (154) and with at least one vacuum source in the present example. In particular, a probe port (330) extends distally from outer cup (302) and into base housing (130), and receives cutter (150) as shown in FIG. 7A. A dynamic seal (332) is provided at the interface of probe port (330) and cutter (150), providing a substantially fluid tight seal even as cutter (150) rotates and translates relative to outer cup (302). A vacuum may be provided to the interior of outer cup (302) via a primary vacuum port (340), which extends upwardly from outer cup (302). Primary vacuum port (340) is positioned and configured to couple with a complementary vacuum port (566) in holster (500) when probe (100) and holster (500) are coupled together. Complementary vacuum port (566) is in fluid communication with a vacuum pump [(566)] (*560*) in holster (500), which is operable to generate a vacuum as will be described in greater detail below. A filter (342) is positioned between primary vacuum port (340) and outer cup (302), in the fluid path of a vacuum between primary vacuum port (340) and the interior of outer cup (302). In some versions, filter (342) comprises a hydrophobic filter. In some other versions, filter (342) comprises a hydrophilic filter. As yet another variation, a combination of a hydrophobic filter and a hydrophilic filter may be used. Alternatively, any other suitable type of filter or combination of filters may be used, including no filter (342) at all if desired. A pair of o-rings (344) also provide a seal between primary vacuum port (340) and the housing of outer cup (302), to substantially prevent leaking at the interface between primary vacuum port (340) and the housing of outer cup (302).

Tissue sample holder (300) of the present example also includes a secondary vacuum port (350), which extends proximally from frame (306). Secondary vacuum port (350) is configured to be coupled with an external vacuum source (e.g., a conventional vacuum pump, etc.) to supplement or substitute the vacuum provided by vacuum pump (560). Various examples of how such a secondary vacuum source may be provided and used with biopsy device (10) are described in U.S. Non-Provisional patent application Ser. No. 12/709,695, entitled "Biopsy Device with Auxiliary Vacuum Source," filed Feb. 22, 2010, the disclosure of which is incorporated by reference herein. As best seen in FIGS. 6-7, a tube (352) extends distally from frame (306) and is in fluid communication with secondary vacuum port (350). It should be understood that a cap or plug (not shown) may be selectively secured to secondary vacuum port (350) to substantially seal secondary vacuum port (350), such as when biopsy device (10) is used without a secondary vacuum source and vacuum pump (560) is the sole source of vacuum.

Figure 7B:
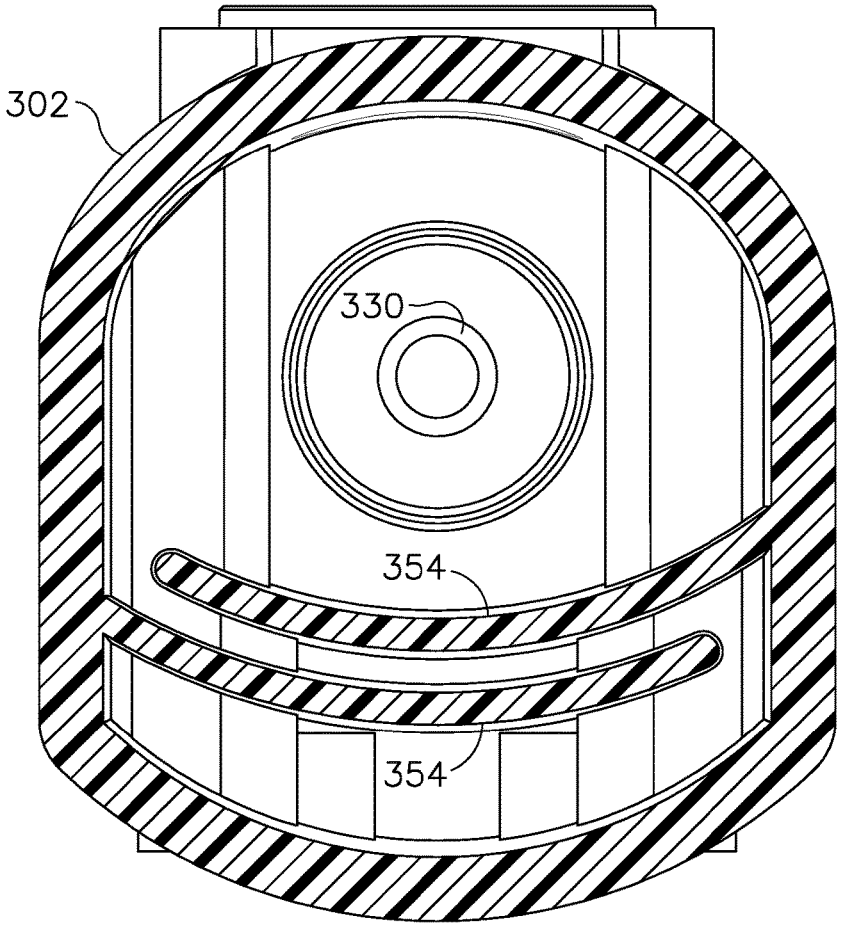
FIG. 7B depicts a cross-sectional end view of the cup of the tissue sample holder of FIG. 6.

As best seen in FIGS. 7A-7B, a set of baffles (354) are provided without outer cup (302), between tube (352) and collection tray (310). In some versions, baffles (354) are configured to allow a vacuum to be communicated through tube (352) to the entire hollow interior of outer cup (302), yet baffles (354) are also configured to "stir" the fluid flow within outer cup (302) to provide a cyclonic suction action. In addition or in the alternative, baffles (354) may provide a tortuous path to reduce the likelihood of fluid within tissue sample holder (300) reaching filter (342) when biopsy device (10) is rotated about the longitudinal axis of biopsy device (10) during use. For instance, if a first set of biopsy samples are collected with port (340) oriented upwardly, fluid may drain below baffles (354), and may substantially remain below at least one of baffles (354) in the event that biopsy device is rotated in either direction such that port (340) is oriented sideways or upwardly during the collection of additional biopsy samples during the same use. Of course, as with other components described herein, baffles (354) may be configured in any other suitable fashion, and may even be omitted if desired. It should also be understood that one or more filters may be provided in or near tube (352), including but not limited to particulate filters, hydrophobic filters, hydrophilic filters, etc. In some other versions, secondary vacuum port (350) is simply omitted altogether. In addition or in the alternative, primary vacuum port (340) and vacuum pump (560) may be omitted if desired.

Tissue sample holder (300) of the present example also includes a guidance funnel (360). Guidance funnel (360) includes a central opening (362) that is configured to align with the axis of cutter lumen (154) and distal port (312) of collection tray (310). Guidance funnel (360) is fixedly secured to a proximal portion of probe port (330), as best seen in FIG. 7. When collection tray (310) is positioned within outer cup (302) and cap (304) is secured to frame (306), the proximal portion of guidance funnel (360) abuts the distal face (364) of collection tray (310). When collection tray (310) and cap (304) are removed from tissue sample holder (300), guidance funnel (360) remains within outer cup (302), secured to the proximal portion of probe port (330). A plurality of openings (366) are formed in the body of guidance funnel (360). Such openings (366) are configured to prevent guidance funnel (360) from being secured to distal face (364) of collection tray (310) like a suction cup, which might otherwise make it more difficult to remove collection tray (310) from outer cup (302). In addition or in the alternative, such openings (366) may be configured to allow fluid (e.g., blood, saline, air, etc.) to fill the space between guidance funnel (360) and collection tray (310), to make greater use of the internal volume of outer cup (302). When collection tray (310) and cap (304) are removed from tissue sample holder (300), guidance funnel (360) may facilitate insertion of a biopsy site marker applier shaft (not shown) into cutter lumen (154) by helping to guide the marker applier shaft to be coaxial with cutter lumen (154). It should therefore be understood that, after one or more biopsy samples are captured by biopsy device (10), and with needle (110) still inserted in tissue, a user may remove collection tray (310) and cap (304) from tissue sample holder (300) then insert a marker applier shaft into cutter lumen (154) via guidance funnel (360) to deploy one or more biopsy site markers to the biopsy site via lateral aperture (114). In addition or in the alternative, guidance funnel (360) may facilitate administration of a pain medication to a biopsy site from a syringe having a catheter-like tube coupled with the distal end of the syringe barrel, by facilitating insertion of the catheter-like tube from the proximal end of biopsy device (10).

Tissue sample holder (300) of the present example is also selectively removable from probe (100). In particular, outer cup (300) includes a pair of latches (370) that selectively engage base housing (130). Latches (370) are resiliently biased to secure tissue sample holder (300) to base housing (130), yet may be deflected to disengage tissue sample holder (300) from base housing (130). Each latch (370) includes a respective button portion (372) to provide such disengagement. In particular, latches (370) may be disengaged from base housing (130) by pressing button portions (372) inwardly toward each other. With button portions (372) depressed inwardly, latches (370) deflect to disengage housing (130), such that tissue sample holder (300) may be pulled proximally to separate tissue sample holder (300) from probe (100). In some versions, vacuum port (340) slides free from outer cup (302), such that vacuum port (340) remains coupled with probe (100) and/or holster (500) when tissue sample holder (300) is pulled free. Alternatively, vacuum port (340), probe (100), and/or holster (500) may be configured to allow vacuum port (340) to be disengaged from probe (100) and/or holster (500) with outer cup (302) when tissue sample holder (300) is pulled free. In some other versions (e.g., those that only rely on an external source coupled with secondary vacuum port (350) for vacuum), vacuum port (340) is omitted entirely. It should also be understood that biopsy device (10) may include one or more features configured to substantially seal the proximal end of cutter (150) when tissue sample holder (300) is removed from biopsy device (10). For instance, such a seal may substantially prevent blood and/or other bodily fluids from exiting the proximal end of cutter lumen (154) when sample holder (300) is removed from biopsy device (10) while needle (110) is still inserted in tissue. Such a seal may also effectively open when tissue sample holder (300) is recoupled with biopsy device (10). Various suitable ways in which such a seal may be provided will be apparent to those of ordinary skill in the art in view of the teachings herein. Similarly, various other suitable ways in which tissue sample holder (300) may be selectively engaged with base housing (130) will be apparent to those of ordinary skill in the art in view of the teachings herein.

As best seen in FIGS. 2, 6, and 7, tissue sample holder (300) of the present example includes a contact (380) that is configured to engage a corresponding contact sensor (520) (which is only shown in FIG. 11) of holster (500) when probe (100) and holster (500) are coupled together. Thus, as will be described in greater detail below, a control module (510) in holster (500) may sense when tissue sample holder (300) is coupled with or decoupled from probe (100), and may control or restrict operation of biopsy device (10) accordingly. Of course, biopsy device (10) may alternatively include a variety of other types of features configured to sense when tissue sample holder (300) is coupled with or decoupled from probe (100). Furthermore, some variations of biopsy device (10) may include a tissue sample holder (300) that is not removable from probe (100).

Tissue sample holder (300) of the present example is configured to hold up to at least ten tissue samples before collection tray (310) must be removed, though it should be understood that tissue sample holder (300) may be configured to hold any other suitable number of tissue samples. In some alternative versions, in lieu of having a stationary collection tray (310), tissue sample holder (300) may have a plurality of trays that are removably coupled with a rotatable manifold, such that the manifold is operable to successively index each tray relative to cutter lumen (154) to separately receive tissue samples obtained in successive cutting strokes of cutter (150). For instance, tissue sample holder (300) may be constructed and operable in accordance with the teachings of U.S. Pub. No. 2008/0214955, entitled "Presentation of Biopsy Sample by Biopsy Device," published Sep. 4, 2008, the disclosure of which is incorporated by reference herein. As another merely illustrative example, tissue sample holder (300) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. Still other suitable ways in which tissue sample holder (300) may be constructed and operable will be apparent to those of ordinary skill in the art in view of the teachings herein.

D. Exemplary Needle Valving Mechanism

Figure 9A:
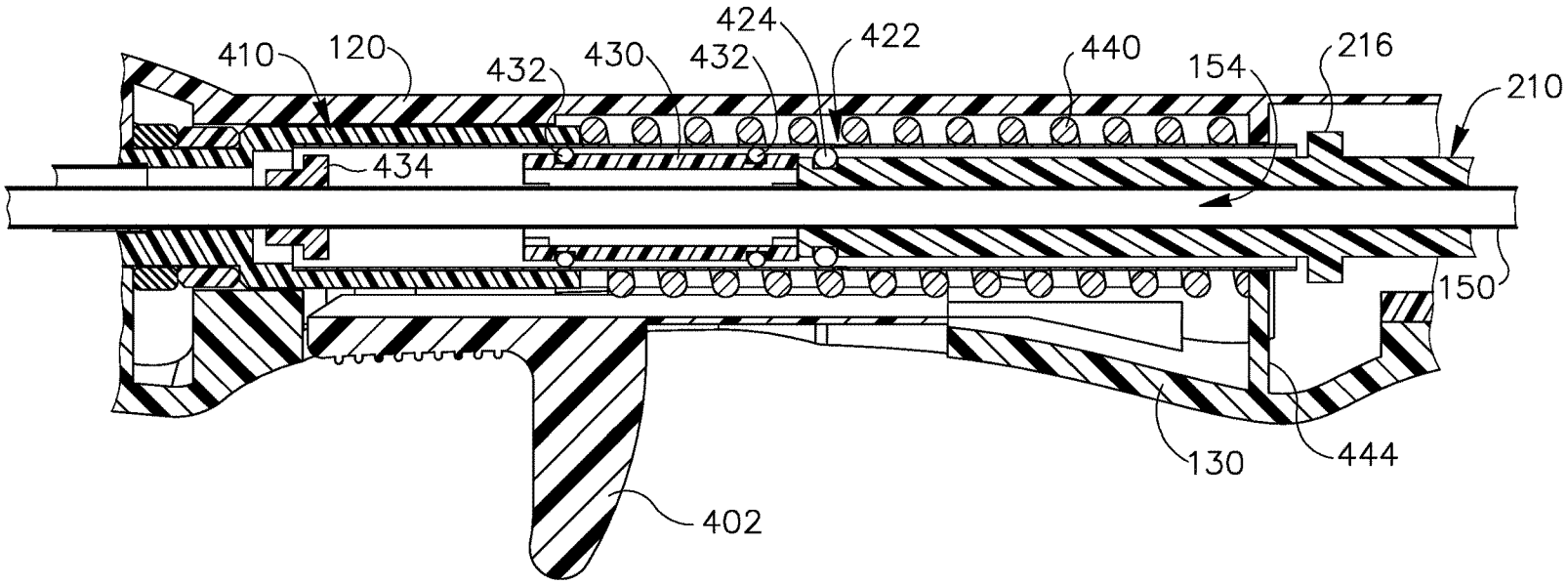
FIG. 9A depicts a partial cross-sectional side view of the needle valving components of FIG. 8, with the cutter in a distal position.
Figure 9B:
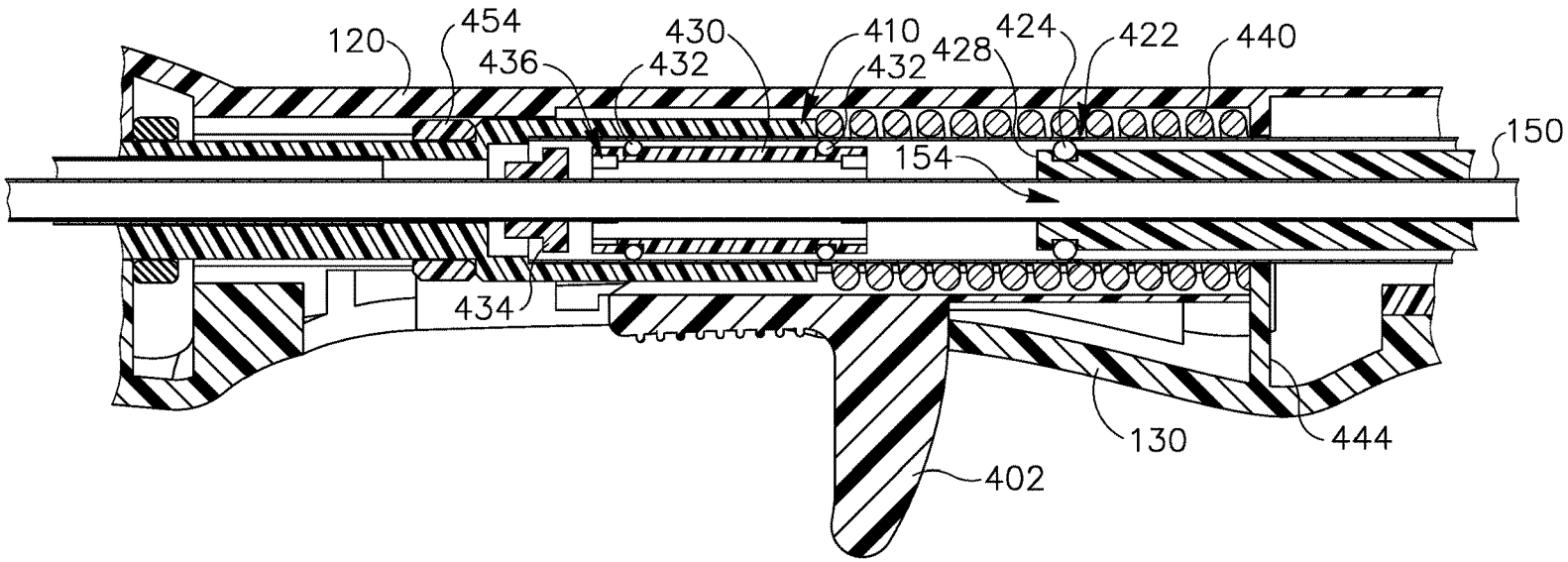
FIG. 9B depicts a partial cross-sectional side view of the needle valving components of FIG. 8, with the cutter in an intermediate position.
Figure 9C:
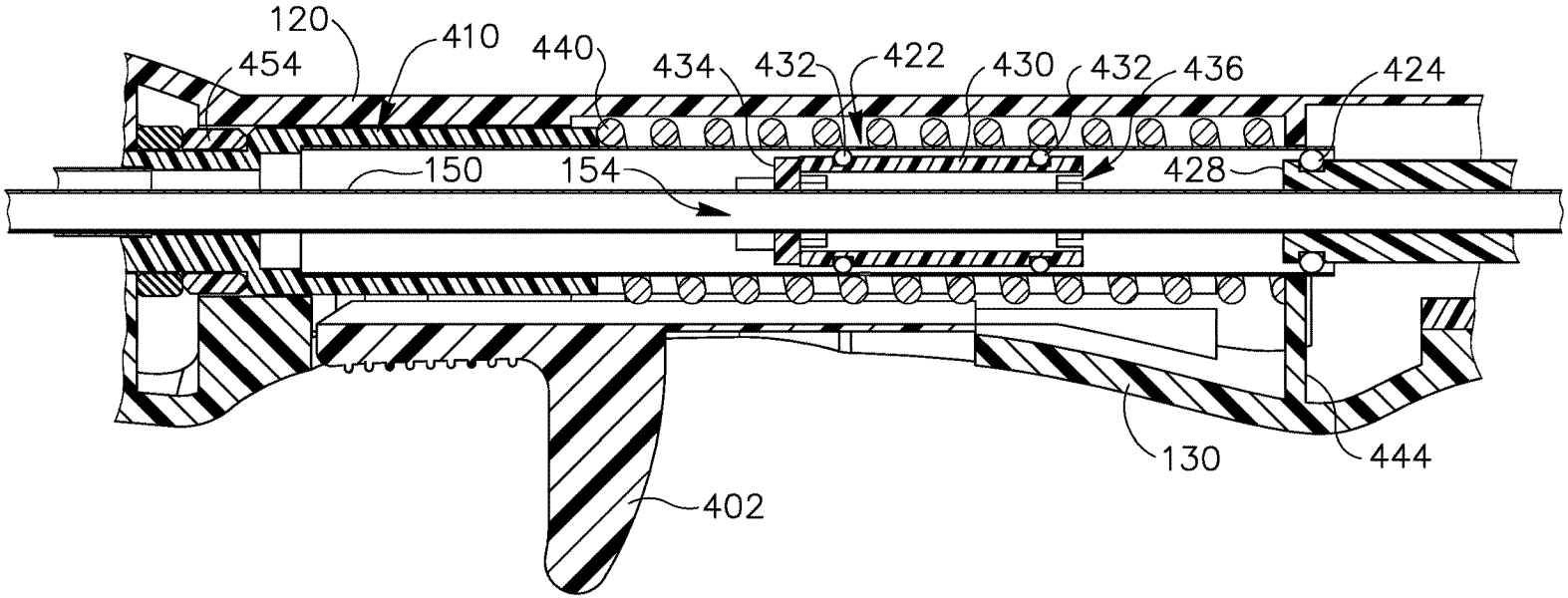
FIG. 9C depicts a partial cross-sectional side view of the needle valving components of FIG. 8, as well as a distal portion of the needle and cutter, with the cutter in a proximal position.

As shown in FIGS. 8-9C, probe (100) further includes components that are operable to selectively vent or seal second lumen (162) of needle (110) relative to atmosphere. These components include a vent sleeve (420) and a shuttle valve slider (430). Vent sleeve (420) is secured relative to chassis (120) and base housing (130), such that vent sleeve (420) does not move during operation of biopsy device (10); while shuttle valve slider (430) translates based on operational movement of cutter (150). A distal portion of vent sleeve (420) is slidably disposed within proximal portion (416) of needle overmold (410). The outer diameter of vent sleeve (420) and the inner diameter of proximal portion (416) of needle overmold (410) are secured together unitarily in the present example, such that vent sleeve (420) and needle overmold (410) translate unitarily. It should also be understood that, even with cutter disposed through vent sleeve (420), the interior of vent sleeve (420) is in fluid communication with second lumen (162) of needle (110) via needle overmold (410). Vent sleeve (420) includes a plurality of transverse openings (422) that are longitudinally co-located with each other and that are equidistantly spaced from each other about the outer perimeter of vent sleeve (420) at their common longitudinal position. Transverse openings (422) provide communication of atmospheric air to the interior of vent sleeve (420) as will be described in greater detail below. As best seen in FIGS. 9A-9C, the proximal end of vent sleeve (420) is sealed by an o-ring (424), which is disposed in an annular recess (426) formed in distal portion (211) of cutter overmold (210). Biopsy device (10) of this example is configured such that o-ring (424) remains positioned within vent sleeve (420) at all times during operation of biopsy device (10), even when cutter (150) is at a proximal position as shown in FIG. 10.

Shuttle valve slider (430) is disposed coaxially about cutter (150), and has an inner diameter permitting shuttle valve slider (430) to longitudinally slide freely relative to cutter (150). Shuttle valve slider (430) also translates relative to vent sleeve (420). A pair of o-rings (432) are positioned at the ends of shuttle valve slider (430), and are configured to seal against the inner surface of vent sleeve (420) yet still permit shuttle valve slider (430) to translate relative to vent sleeve (420). Shuttle valve slider (430) is longitudinally positioned between the distal end (428) of cutter overmold (210) and an annular stop member (434), which is unitarily secured to cutter (150) by a friction fit. Shuttle valve slider (430) defines an inner diameter that is greater than the outer diameter defined by cutter (150), such that a gap is provided between the outer diameter of cutter (150) and the inner diameter of shuttle valve slider (430) along the length of the interior of shuttle valve slider (430). Such a gap is sufficient to provide longitudinal fluid communication (e.g., atmospheric air, etc.) between the outer diameter of cutter (150) and the inner diameter of shuttle valve slider (430). In addition, the distal and proximal ends of shuttle valve slider (430) include notches (436) formed therein, providing an appearance similar to that of a castellated nut or castle nut.

The proximal end of shuttle valve slider (430) is also configured to be engaged by distal end (428) of cutter overmold (210), such that cutter overmold (210) may push shuttle valve slider (430) distally as described below. Notches (436) at the proximal end of shuttle valve slider (430) are configured to provide fluid communication to the interior of shuttle valve slider (430), even as distal end (428) of cutter overmold (210) engages the proximal end of shuttle valve slider (430). Similarly, the distal end of shuttle valve slider (430) is configured to be engaged by stop member (434), such that stop member (434) may push shuttle valve slider (430) proximally as described below. Notches (436) at the distal end of shuttle valve slider (430) are configured to provide fluid communication to the interior of shuttle valve slider (430), even as stop member (434) engages the distal end of shuttle valve slider (430).

As described elsewhere herein, cutter (150) is configured to rotate and translate relative to base housing (130), while vent sleeve (420) remains substantially stationary relative to base housing (130). As noted above, cutter overmold (210) and stop member (434) translate unitarily with cutter (150). In addition, stop member (434) and shuttle valve slider (430) are configured such that stop member (434) may push shuttle valve slider (430) proximally when stop member (434) is engaged with shuttle valve slider (430) (see, e.g., FIG. 9C); while cutter overmold (210) and shuttle valve slider (430) are configured such that cutter overmold (210) may push shuttle valve slider (430) distally when cutter overmold (210) is engaged with shuttle valve slider (430) (see, e.g., FIG. 9A). Shuttle valve slider (430) may thus translate within vent sleeve (420) in accordance with translation of cutter (150) relative to base housing (130). However, the distance between distal end (428) of cutter overmold (210) and the proximal end of stop member (434) is greater than the length of shuttle valve slider (430), such that there is a degree of "lost motion" between shuttle valve slider (430) and cutter (150) as cutter (150) translates in the present example. In other words, shuttle valve slider (430) remains substantially stationary during certain stages of a cutter (150) actuation stroke (see, e.g., FIGS. 9A-9B), such that shuttle valve slider (430) only translates when cutter (150) starts closely approaching the distal-most position travelling from the proximal-most position; and when cutter (150) starts closely approaching the proximal-most position (see, e.g., FIG. 9C).

As noted above, openings (422) of vent sleeve (420) communicate with ambient air; and shuttle valve slider (430) is operable to selectively vent second lumen (162) to atmosphere. In particular, shuttle valve slider (430) remains distal to openings (422) when cutter (150) is at a distal-most position (see, e.g., FIG. 9A); when cutter (150) is transitioning between the distal-most position and the proximal-most position (see, e.g., FIG. 9B); and at latter stages of cutter (150) transitioning from the proximal-most position to the distal-most position. During these stages of operation, second lumen (162) is exposed to ambient air via openings (422) in vent sleeve (422), notches (436) in shuttle valve slider (430), the gap between the inner diameter of shuttle valve slider (430) and the outer diameter of cutter (150), and the portion of the interior of vent sleeve (420) that is distal to shuttle valve slider (430). However, shuttle valve slider (430) and o-rings (432) substantially seal second lumen (162) relative to openings (422) when cutter (150) is in a proximal position, such as is shown in FIG. 9C. In particular, when cutter (150) moves to the proximal position, stop member (434) pushes shuttle valve slider (430) proximally such that openings (422) are longitudinally positioned between o-rings (432). O-rings (432) thus substantially seal off second lumen (162) relative to openings (422) when openings (422) are between o-rings (210). When cutter (150) begins moving again distally toward the distal-most position, shuttle valve slider (430) remains at this proximal position momentarily, continuing to substantially seal second lumen (162) relative to openings (422), until distal end (428) of cutter overmold (210) engages the proximal end of shuttle valve slider (430) and begins pushing shuttle valve slider (430) distally to the point where the proximal-most o-ring (432) is moved distal to openings (422). Once the proximal-most o-ring (432) moves distal to openings (422), second lumen (162) is again vented to atmosphere as noted above. Thus, the valve mechanism of the present example substantially seals off second lumen (162) relative to atmosphere when cutter (150) is at a proximal position and when cutter (150) is at initial stages of distal advancement; while venting second lumen (162) to atmosphere when cutter (150) is at other positions.

It should be understood that, as with other components described herein, the valving components described above may be varied, modified, substituted, or supplemented in a variety of ways; and that a valve mechanism may have a variety of alternative features, components, configurations, and functionalities. Suitable alternative versions, features, components, configurations, and functionalities of a valve mechanism will be apparent to those of ordinary skill in the art in view of the teachings herein. It should also be understood that, in some versions of biopsy device (10) that lack a vacuum pump (566) (e.g., vacuum only provided by external vacuum pump through secondary vacuum port (350), etc.), valving functions may be performed by valve components located between biopsy device (10) and an external vacuum source, such that biopsy device (10) may lack a valve mechanism altogether.

E. Exemplary Needle Firing Mechanism

Biopsy device (10) of the present example is operable to selectively fire needle (110) distally relative to chassis (120) and relative to base housing (130) through a needle firing mechanism (400). A user may wish to employ needle firing mechanism (400) in instances where needle (110) is encountering dense tissue or under other circumstances. Of course, biopsy device (10) may also be operated without ever using needle firing mechanism (400). As shown in FIGS. 8 and 10A-10E, needle firing mechanism (400) of the present example includes a coil spring (440), a catch (450), and an arming slider (460). Coil spring (440) is positioned coaxially about cutter (150) and vent sleeve (420). The distal end of coil spring (440) bears against the proximal end (442) of needle overmold (410); while the proximal end of coil spring (440) bears against an integral boss (444) of base housing (130). Coil spring (440) is resiliently biased to urge needle overmold (410) (and, hence, needle (110)) distally. Distal movement of needle (110) is restricted by a bumper washer (446), which abuts a pair of bosses (448) formed in base member (130). Bumper washer (446) of the present example is formed of an elastomeric material that is configured to absorb at least some of the shock created by sudden distal movement of needle overmold (410) when needle (110) is fired distally. Of course, bumper washer (446) may be substituted or supplemented with a variety of other components (e.g., spring, etc.); or may be omitted altogether.

Catch (450) of needle firing mechanism (400) comprises an elongate beam (452), an annular member (454) at the distal end of elongate beam (452), and a transverse projection (456) at the proximal end of elongate beam (452). Elongate beam (452) is formed of a resilient material such as plastic, and is biased to assume a bowed configuration as shown in FIGS. 10A and 10E in some versions. In some other versions, elongate beam (452) is resiliently biased to assume a substantially straight configuration, but is capable to being bent to the bowed configuration shown in FIGS. 10A and 10E. Annular member (454) is coaxially disposed about distal portion (412) of needle overmold (410), proximal to bumper washer (446). The inner diameter of annular member (454) is less than the outer diameter of proximal portion (416) of needle overmold (410). Accordingly, when catch (450) is pulled proximally as described in greater detail below, annular member (454) pulls needle (110) from a distal position to a proximal position, against the distal bias provided by spring (440). Similarly, as needle (110) is fired distally from a proximal position to a distal position, proximal portion (416) of needle overmold (410) pushes annular member (454) (and, hence, catch (450)) distally. Transverse projection (456) projects inwardly toward other components of needle firing mechanism (400), and is configured to selectively engage distal flange (216) of cutter overmold (210) as will be described in greater detail below.

A pin (458) is inserted through the proximal end of elongate beam (452), near the position from which transverse projection (456) projects. Pin (458) extends upwardly and downwardly from elongate beam (452). A lower portion of pin (458) is disposed in a track (470) that is formed in base housing (130). An upper portion of pin is disposed in a corresponding track (not shown) that is formed in the underside of chassis (120) and that has a shape complementing the shape of track (470). The portion of chassis (120) presenting this corresponding track may include reinforcement to provide additional strength to bear stresses imposed by pin (458) during operation of needle firing mechanism (400). Track (470) in base housing (130) includes an inner portion (472) and an outer portion (474). Viewed from the top down and from the bottom up, inner portion (472) runs along a path that is substantially parallel to the longitudinal axis of cutter (150) and various other components; while outer portion (474) runs along a path that includes a curved portion to allow transverse projection (456) to clear distal flange (216) of cutter overmold (210) as will be described in greater detail below. In other words, inner portion (472) does not stray transversely away from or toward the longitudinal axis of cutter (150) along a horizontal plane passing through inner portion (472); while outer portion (474) does stray transversely away from the longitudinal axis of cutter (150) along a horizontal plane passing through outer portion (474).

Inner portion (472) and outer portion (474) are generally located at different heights in this example. In particular, in some versions, a proximal part of outer portion (474) runs at a generally lower (474) height (e.g., in relation to chassis (120)) than the proximal part of inner portion (472). In the distal part of track (470), the height transition between portions (472, 474) is substantially smooth. In particular, as pin (458) travels from outer portion (474) to and along inner portion (472), pin (458) ascends a generally gradual incline. However, in the proximal portion of track (470), a step (476) separates inner portion (472) from outer portion (474). Thus, as pin (458) transitions back from inner portion (472) to outer portion (474), pin (458) jumps down step (476) to reach outer portion (474) of track (470). In the present example, step (476) is formed at an angle that is oblique to the longitudinal axis defined by cutter (150), along a horizontal plane that runs through track (470), to further promote pin (458) jumping down step to reach outer portion (474) as pin (458) reaches a proximal-most position. In some versions, outer portion (474) of track (470) defines an incline ascending upwardly toward chassis (120) as outer portion (474) progresses from the proximal end of track (470) to the distal end of track (470). It should therefore be understood that pin (458) may ascend upwardly toward chassis (120) as it travels proximally from the distal end of inner portion (472) to the proximal end of inner portion (472), then jump down step (476) when it transitions to outer portion (474), then ascend upwardly again toward chassis (120) as it travels distally from the proximal end of outer portion (474) to the distal end of outer portion (474). Pin (458) may encounter another step (not shown) at the distal end of outer portion (474), to jump down to reach the distal end of inner portion (474). Of course, track (470) may alternatively have any other suitable features or configurations.

As noted above, beam (452) is resiliently biased to assume a bent configuration, which in turn provides a resilient bias for pin (458) to be disposed in outer portion (474) of track (470). Nevertheless, while pin (458) travels proximally from the distal end of inner portion (472) toward the proximal end of inner portion (472), track (470) is configured to keep pin (458) in inner portion (472) until pin (458) reaches the proximal end of inner portion (472). Once pin (458) reaches the proximal end of inner portion (472), the resilient urging of beam (452), as well as the angled orientation of step (476), causes pin (458) to jump down into outer portion (474) of track (470). It should also be understood that the upward travel of pin (458) along inner portion (472) of track (470) may further cause vertical deflection in beam (452), which may provide a downward bias of beam (452) to further urge pin (458) downward into inner portion (472) of track (470) when pin (458) reaches the proximal end of inner portion (472).

Arming slider (460) of the present example is operable to deflect beam (452) inward, to selectively transition pin (458) from outer portion (474) to inner portion (472) at the distal end of track (470). Arming slider (460) is slidable relative to base housing (130) and comprises a finger grip (402) protruding downwardly from base housing (130). An inner sidewall (462) is configured and positioned to push inwardly against beam (452) to deflect beam (452) inwardly as slider (460) is slid proximally. Slider (460) is also configured to move upwardly toward chassis (120) in the present example. Slider (460) includes a set of resilient angled tabs (464) that are configured to bear against the underside of chassis (120), biasing slider (460) downwardly away from chassis (120). In addition, a coil spring [(470)] (*469*) is positioned about a post (466) of slider (460), and bears against a boss (473) in base housing (130). Coil spring [(470)] (*469*) is resiliently biased to urge slider (460) to a distal position. Being movable upwardly toward chassis (120), slider (460) is further operable to push upwardly on beam (452), thereby facilitating transition of pin (458) from outer portion (474) of track (470) to inner portion (472) of track (470). Such capability may be useful in versions where beam (452) is resiliently biased to assume a downwardly bent configuration in addition to being resiliently biased to assume an outwardly bent configuration; and/or in versions where the transition from outer portion (474) of track (470) to inner portion (472) of track (470) includes a step or is otherwise not very gradual at the distal end of track (472). In some versions, base housing (130) includes a stepped track that substantially prevents arming slider (460) from being slid proximally without slider (460) also being simultaneously pushed upwardly toward chassis (120). Such a stepped track (or other component/feature/etc.) may serve as a lockout preventing inadvertent proximal movement of slider (460) relative to base housing (130).

FIGS. 10A-10E show needle firing mechanism (400) at various stages of operation, which will be described below. In particular, FIG. 10A shows needle firing mechanism (400) in a ready to arm configuration. In this configuration, cutter (150) is in a distal position, such that distal flange (216) of cutter overmold (210) is located at a longitudinal position that is distal to (yet lateral to) the longitudinal position of transverse projection (456) of catch (450). The resilient bias of beam (452) provides beam (452) with an outwardly bent configuration, with pin (458) disposed in outer portion (474) of track (474) such that transverse projection (456) is positioned away from distal flange (216). In some versions, needle (110) is inserted in tissue (e.g., a human breast, etc.) when biopsy device (10) is in this configuration. It should be understood that, at the stage of operation shown in FIG. 10A, other components of biopsy device (10) of the present example are in the positions and configurations shown in FIGS. 5A and 9A.

FIG. 10B shows needle firing mechanism (400) in an armed and ready to retract configuration. In particular, a user has slid arming slider (460) to a proximal position, such as by pulling proximally on finger grip (402) or otherwise. In some versions, the user has also pushed upwardly to move slider (460) toward chassis (120) in addition to pulling proximally on finger grip (402) to slide arming slider (460) to a proximal position. Cutter (150) has not moved between the stages shown in FIGS. 10A-10B, such that the longitudinal position of distal flange (216) has remained consistent at this stage. As seen in FIG. 10B, inner sidewall (462) has pushed inwardly against beam (452) to deflect beam (452) inwardly as slider (460) was slid proximally. This inward deflection of beam (452) (and upward deflection of beam (452), in some versions) has moved transverse projection (456) inwardly to an armed position. With transverse projection (456) in this armed position, pin (458) has moved to the inner portion (472) of track (470) and transverse projection (456) is now located adjacent to and just proximal to distal flange (216) of cutter overmold (210). In some versions, there is no change in height between outer portion (474) of track (470) and inner portion (472) of track (470) at this distal end of track (470). In some other versions, while moving from outer portion (474) of track (470) to inner portion (472) of track (470), pin (458) traverses a slight incline (or a step, in some versions) to move slightly upwardly toward chassis (130).

FIG. 10C shows needle firing mechanism (400) transitioning to a retracted and loaded or ready to fire configuration. In particular, cutter actuation mechanism (200) has been activated to retract cutter (150) proximally, which in turn has retracted distal flange (216) proximally. In some versions, cutter (150) is not yet in a fully proximal position at this stage. In some other versions, cutter (150) is in a fully proximal position at this stage. As can be seen in FIG. 10C, the proximal retraction of cutter (150) and distal flange (216) has moved catch (450) proximally due to engagement between distal flange (216) and transverse projection (456). This proximal movement of catch (450) has also moved needle overmold (410) proximally due to engagement between annular member (454) of catch (450) and proximal portion (416) of needle overmold (410). With needle overmold (410) moved proximally and being unitarily secured to needle (110), needle (110) has also been moved to a proximal position relative to base housing (130) at this stage. Spring (440) is now in a more compressed state, resiliently urging needle overmold (410) (and, hence, needle (110)) distally. It should be understood that, at the stage of operation shown in FIG. 10C, other components of biopsy device (10) of the present example are in the positions and configurations shown in FIGS. 5B and 9B. It should also be understood that needle (110) and cutter (150) have translated proximally together during the transition between the stage depicted in FIG. 10B and the stage depicted in FIG. 10C.

FIG. 10D shows needle firing mechanism (400) at a stage where needle firing mechanism (400) is in a retracted and ready to fire configuration. In particular, cutter actuation mechanism (200) has continued to retract cutter (150) proximally, which in turn has retracted distal flange (216) further proximally. At this stage, catch (450) has been retracted to a point where pin (458) has jumped down step (476) to transition from inner portion (472) of track (470) to outer portion (474) of track (470). Also at this stage, proximal retraction of cutter (150) is ceased at least temporarily. Since some versions of biopsy device (10) permit biopsy device (10) to be used regardless of whether needle firing mechanism (400) is also used, it may be beneficial for biopsy device (10) to have intelligence permitting control components of biopsy device (10) to discern whether needle firing mechanism (400) is being used or not and to operate cutter actuation mechanism (200) accordingly. That is, such intelligence may determine whether retraction of cutter (150) should cease when cutter (150) reaches the position shown in FIG. 10D (i.e., in cases where needle firing mechanism (400) is being used by the user) or if cutter (150) should continue retracting without cessation when cutter (150) reaches the position shown in FIG. 10D (i.e., in cases where needle firing mechanism (400) is not being used by the user). For instance, as described in greater detail below, holster (500) includes a control module (510) that is in communication with motor (528) and with an encoder sensor (526), which is configured to monitor movement produced by motor (528). Control module (510) may include a logic configured to monitor the current profile (and/or other performance related characteristic) of motor (528) with respect to the longitudinal position of cutter (150) as discerned by data from encoder sensor (526), in relation to a baseline current profile. When needle firing mechanism (400) is being used by the user, the work required to compress spring (440) may impose an additional load on motor (528) that can be detected based on the amount of current drawn by motor (528) with respect to the longitudinal position of cutter (150), as compared to a baseline current that might be expected when needle firing mechanism (400) is not being used by the user. Control module (510) may thus cease retraction of cutter (150) when cutter reaches the position shown in FIG. 10D when that additional load is detected.

As another merely illustrative example, one or more sensors (e.g., hall effect sensor, proximity sensor, etc.) within probe (100) may be used to detect whether needle firing mechanism (400) is being used by the user, and such one or more sensors may provide such data to control module (510) to alert control module (510) to cease retraction of cutter (150) when cutter reaches the position shown in FIG. 10D. Various forms that such sensors may take as well as various ways in which such sensors may communicate with control module (510) will be apparent to those of ordinary skill in the art in view of the teachings herein. Regardless of the structures and methods used to determine whether needle firing mechanism (400) is being used by the user, it may also be desirable in versions where cutter (150) retraction is ceased at the stage shown in FIG. 10D to notify the user of biopsy device (10) that needle firing mechanism (400) is cocked and ready to fire. Such notification may be provided through various components of holster (500) (e.g., speaker (522), LEDs (524), etc.), through one or more mechanical components that provide a loud audible click or other form of audible feedback, etc. Needle firing mechanism (400) may then be fired when the user activates a button (516) on holster (500). Such activation may also automatically continue a sampling cycle by completing retraction of cutter (150) and then advancing cutter (150) distally to sever a tissue sample. Alternatively, control module (510) may be configured to require a first activation of button (516) to fire needle firing mechanism (400) after needle firing mechanism (400) has reached the stage shown in FIG. 10D; and a second activation of button (516) to continue/complete a sampling cycle. This may allow needle (110) to be fired repeatedly during a single insertion of needle (110) in tissue before a tissue sample is captured by cutter (150).

When the user activates button (516) to fire needle firing mechanism (400), control module (510) activates cutter actuation mechanism (200) to reverse motion of cutter (150) to advance cutter (150) slightly distally in order to facilitate disengagement of transverse projection (456) from distal flange (216) once needle firing mechanism (400) has reached the configuration shown in FIG. 10D. It should be understood that, in some such versions, step (476) keeps pin (458) in outer portion (474) of track (470) even if cutter (150) is advanced slightly at this stage. It should also be understood that, with pin (458) being positioned in outer portion (474), and with transverse projection (456) disengaged from distal flange (216), beam (452) may return to a bent configuration (e.g., in versions where beam (452) is resiliently biased to assume a bent configuration, etc.) or otherwise be bent to assume a bent configuration (e.g., in versions where beam (452) is resiliently biased to assume a straight configuration, etc.). It should also be understood that the oblique orientation of step (476) may encourage beam (452) to transition to a bent configuration by providing a transversely located cam surface against pin (458). In addition to or in lieu of advancing cutter slightly distally in order to facilitate disengagement of transverse projection (456) from distal flange (216) once needle firing mechanism (400) has reached the configuration shown in FIG. 10D, a resilient outward bias of beam (452) alone may suffice to disengage transverse projection (456) from distal flange (216) once needle firing mechanism (400) has reached the configuration shown in FIG. 10D.

As can also be seen in FIG. 10D, the user of biopsy device (10) has released finger grip (402) of arming slider (460), allowing arming slider (460) to return to a distal position under the resilient distal urging of spring (470). In some versions, and as discussed above, biopsy device (10) may provide an audio, visual, and/or tactile indication to the user indicating that needle firing mechanism (400) is ready to fire. This may alert the user to release arming slider (460) to the extent that the user has not already released arming slider (460) at this stage. In some versions, arming slider (460) includes a chamfer or similar feature at the proximal end of inner sidewall (462), which substantially prevents re-arming of firing mechanism (400) if arming slider (460) is not released between tissue sampling cycles (i.e., cutting strokes/cycles of cutter (150)).

In the present example, with transverse projection (456) disengaged from distal flange (216) (shortly after the moment depicted in FIG. 10D), the resilient bias of spring (440) suddenly urges needle overmold (410) distally relative to base housing (130), thereby firing needle (110) distally. It should be understood that cutter (150) is still not yet fully retracted at this stage. It should also be understood that needle (110) translates distally relative to cutter (150), in addition to translating distally relative to base housing (130), when needle (110) is fired distally by needle firing mechanism (400). FIG. 10E shows needle firing mechanism (400) upon firing of needle (110). In particular, and as noted above, disengagement between transverse projection (456) and distal flange (216) has allowed spring (440) to fire needle (110) to a distal position. During the transition from FIG.

10D to FIG. 10E (e.g., during actual firing of needle (110)), pin (458) has traversed the full path of outer portion (472) of track (470), returning to the distal region of track (470). It should be understood that, after needle (110) is fired by firing mechanism (400), cutter actuation mechanism (200) may suspend movement of cutter (150) in the present example, in addition to or in lieu of suspending movement of cutter (150) when needle firing mechanism (400) is cocked and ready to fire as described above with reference to FIG. 10D. In some versions, cutter actuation mechanism (200) may continue retracting cutter (150) proximally after suspending movement of cutter (150) for a suitable duration (e.g., after predetermined duration, until the user again actuates a button (516) of holster (500), etc.). Alternatively, cutter actuation mechanism (200) may continue to retract cutter (150) proximally after needle (110) is fired by firing mechanism (400), without providing at least temporary suspension of movement of cutter (150). It should be understood that, at the stage of operation shown in FIG. 10E, other components of biopsy device (10) of the present example are in the positions and configurations shown in FIGS. 5C and 9C.

In the present example, vent sleeve (420) translates when needle firing mechanism (400) is cocked and fired. In particular, needle overmold (410) pushes vent sleeve (420) proximally as needle firing mechanism (400) pulls needle (110) proximally (see FIG. 9B). Needle overmold (410) pulls vent sleeve (420) distally as needle firing mechanism (400) pushes needle (110) distally (see FIG. 9C). When biopsy device (10) is used without firing needle (110) (e.g., when needle firing mechanism (400) is present but not used by the user of biopsy device (10)), vent sleeve (420) simply remains in the distal position (see FIG. 9A). It should be understood that the valving components described above will operate in the same manner as described above regardless of whether a user decides to operate needle firing mechanism (400). In other words, second lumen (162) will be vented or sealed relative to atmosphere at the same stages of cutter (150) actuation regardless of whether needle firing mechanism (400) is used.

It should be understood that the above described components, features, configurations, and operabilities of needle firing mechanism (400) are merely illustrative. Any of these components, features, configurations, and operabilities may be varied, modified, substituted, supplemented, or even omitted as desired. Various other suitable components, features, configurations, and operabilities that may be incorporated into needle firing mechanism (400) will be apparent to those of ordinary skill in the art in view of the teachings herein. It should also be understood that various other types of devices, including but not limited to any of the biopsy devices described in the references that are cited herein, may be modified to include a needle firing mechanism (400).

II. Exemplary Holster

A. Exemplary Electrical Components of Holster

Figure 11:
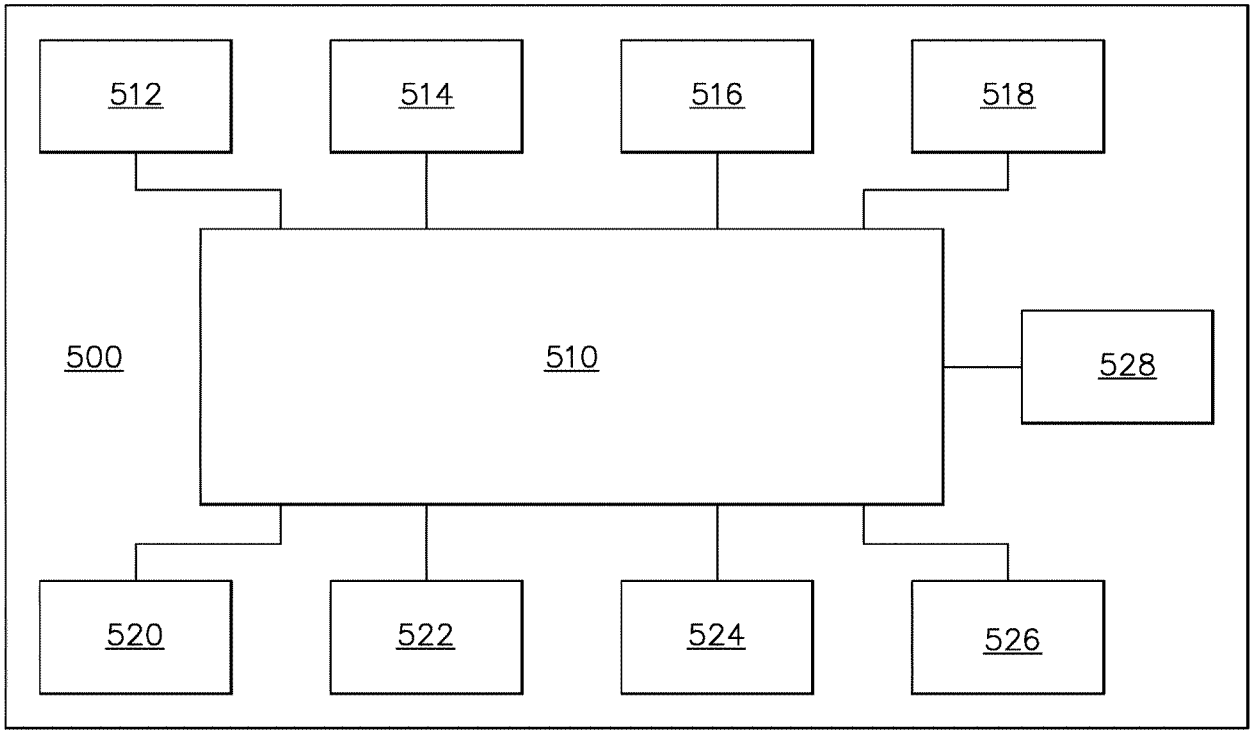
FIG. 11 depicts a schematic diagram showing components of the holster portion of the biopsy device of FIG. 1.
Figure 12:
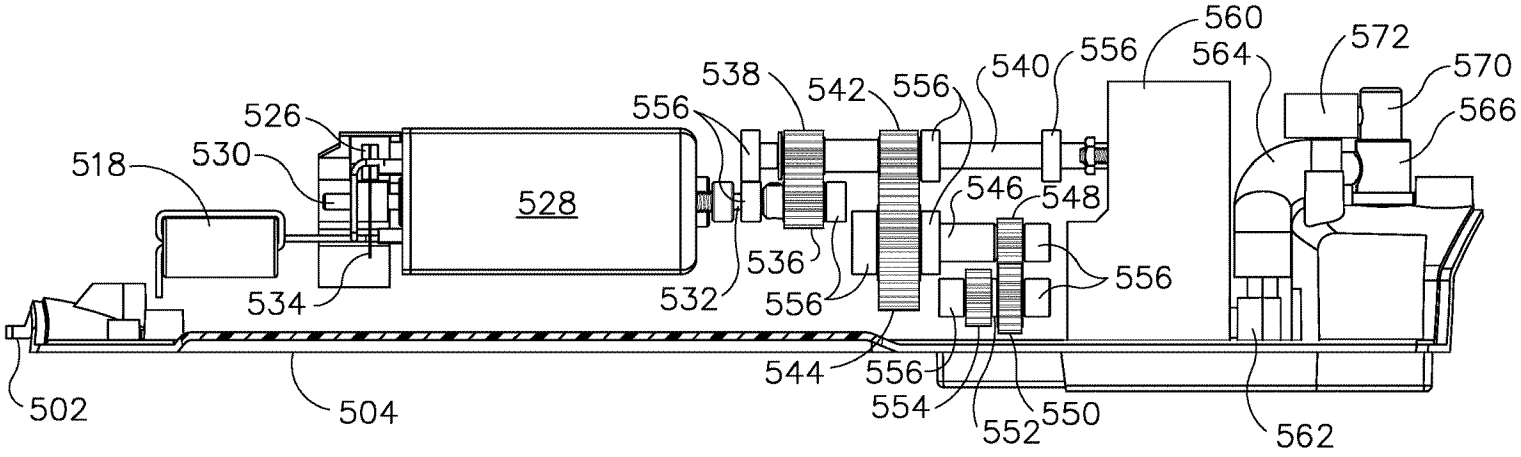
FIG. 12 depicts a side elevational view of the holster of FIG. 11, with housing components and other components removed, showing a motor and drive components.

FIG. 11 shows various electrical and electromechanical components that are incorporated into holster (500) of biopsy device (10) of the present example. It should be understood that each of these components is merely illustrative, and that any of these components may be modified, varied, substituted, supplemented, or even omitted, as desired. As shown in FIG. 11, holster (500) of the present example includes a control module (510), a battery (512), an accelerometer (514), buttons (516), charging circuitry (518), a tissue sample holder sensor (520), a speaker (522), LEDs (524), an encoder sensor (526), and a motor (528). Control module (510) essentially serves as a hub for the other components (512, 514, 516, 518, 520, 522, 524, 526, 528), as all of the other components (512, 514, 516, 518, 520, 522, 524, 526, 528) are in communication with control module (510). As shown in FIGS. 1-2 and 12, holster (500) further comprises a chassis (504), an upper housing (506), and a vacuum pump (560). Each of these components will be described in greater detail below, while other suitable components for holster (500) will be apparent to those of ordinary skill in the art in view of the teachings herein.

While control module (510) is referred to in the singular, it should be understood that control module (510) may comprise a plurality of components and even a plurality of separate control modules. For instance, control module (510) may comprise a plurality of circuit boards, one or more storage devices configured to store data, and/or a variety of microprocessors, etc. In addition, control module (510) may include one or more wireless communication technologies (e.g., Bluetooth technology, etc.) that are operable to communicate with smart phones, foot pedal actuation means, keypads, etc. Various suitable components, features, and configurations that may be employed to form control module (510) will be apparent to those of ordinary skill in the art in view of the teachings herein.

Battery (512) of the present example comprises a rechargeable battery (e.g., nickel cadmium, lithium ion, lithium polymer, etc.). Just like control module (510) and various other components described herein, while battery (512) is referred to in the singular, it should be understood that more than one battery (512) may be incorporated into holster (500). Battery (512) is configured to provide power to motor (528) to operate cutter actuation mechanism (200). For instance, battery (512) may provide any suitable voltage, and may be configured to provide power for at least five biopsy procedures or any other suitable number of procedures before requiring a recharge or replacement. Charging circuitry (518) in holster (500) is configured to recharge battery (512). For instance, holster (500) may be selectively coupled with a docking station to enable charging circuitry (518) to recharge battery (512). Such charging may be provided through contact between complementary exposed metal contacts (not shown) of the docking station and holster (500), through inductive charging components, and/or in any other suitable fashion. It should also be understood that charging circuitry (518) may be configured to monitor the charge level of battery (512). In some such versions, charging circuitry (518) may be configured to drive a battery charge indicator to constantly show the charge level of battery (512), to simply provide an indication (e.g., through speaker (522) and/or LEDs (524), etc.) when the charge level of battery (512) falls below a threshold, and/or provide any other suitable type of notification. Of course, battery (512) may be non-rechargeable, if desired. Furthermore, holster (500) may use an external source (e.g., conventional AC power source or piece of capital equipment, etc.) to power motor (528), in addition to or in lieu of using battery (512). It should also be understood that biopsy device (10) may use an external source to drive cutter actuation mechanism (200) (e.g., may omit motor (528) and use speedometer cables from a remote drive source, use pneumatic components driven by pressurized air, etc.).

In some versions (e.g., where battery (512) is charged through electrical contacts that contact complementary contacts in a charging station, etc.), charging circuitry (518) is omitted and a balun type of transformer is used in its place. Of course, a balun transformer may also be used in versions where battery (512) is charged inductively instead of being charged through electrical contacts, in versions where battery (512) is omitted and biopsy device (10) receives power in some other fashion, etc. In some versions where a balun transformer is used, the balun may convert electrical signals from balanced to unbalanced and/or vice versa. Such a balun may be coupled with motor (528), either directly and/or through control module (510). In addition or in the alternative, such a balun may be coupled with encoder sensor (526) and/or other components of holster (500). Of course, as with other components described herein, a balun may be substituted, supplemented, or even omitted, as desired.

Accelerometer (514) is yet another component that is referred to in the singular but may in fact comprise several separate accelerometers. For instance, some versions of holster comprise three accelerometers (514), each being configured and positioned to sense movement in a respective direction. Movement data from accelerometer (514) may be used to provide both automated power down of holster (500) when holster (500) is not moved for a certain time period and/or to automatically power on holster (500) when holster (500) is moved. For instance, control module (510) may include a logic configured to power down holster (500) and at least substantially cease consumption of power from battery (512) if accelerometer (514) fails to indicate movement of holster (500) over a period of approximately 10 minutes. Any other suitable inactivity duration threshold may be used. This logic may also receive input from charging circuitry (518) to ensure that holster (500) is not fully powered down when battery (512) is being charged (e.g., by a docking station, etc.), even if holster (500) is not moved beyond the inactivity duration threshold while holster (500) is charging. Accelerometer (514) may also be used to detect the orientation of biopsy device (10), and control module (510) may include a logic configured to modify operation of biopsy device (10) based at least in part on orientation data from accelerometer (514). For instance, control module (510) may be configured to stop operation of motor (528) (and, hence, vacuum pump (560) when biopsy device (10) is held in an upside-down orientation (e.g., with holster (500) positioned vertically below probe (100)) beyond a certain threshold duration. Such cessation of vacuum pump (560) operation may reduce the likelihood that filter (342) becomes saturated with bodily fluids. Other suitable ways in which accelerometer (514) may be used will be apparent to those of ordinary skill in the art in view of the teachings herein. It should also be understood that, as with various other components described herein, accelerometer (514) may simply be omitted if desired.

Buttons (516) are operable to selectively activate motor (528) to drive cutter actuation mechanism (200). Buttons (516) may comprise thin film switches, capacitive switches, spring-loaded mechanical buttons, and/or any other suitable type of user input feature. As shown in FIG. 1, a plurality of buttons (516) are provided at different positions on holster (500). Having buttons (516) at various positions may facilitate use of biopsy device (10) using different grip styles, which may vary depending on the user's preference and/or based on the angle at which needle (110) is inserted into tissue, etc. In some versions, any one of buttons (516) may be used at any given time, and pressing any button (516) will provide the same result as pressing any other button (516). In some other versions, once one button (516) is pressed (e.g., pressed once, pressed and held down for a certain duration, or pressed twice in rapid succession, etc.), a logic in control module (510) identifies that button (516) as the active button (516) and all other buttons (516) are deactivated. Of course, each button (516) may be assigned to provide a different function. For instance, one button (516) may be assigned to initiate a tissue sampling cycle when activated, while another button (516) may be assigned to perform a clear probe cycle. Examples of such cycles are described in U.S. Pub. No. 2008/0214955, entitled "Presentation of Biopsy Sample by Biopsy Device," published Sep. 4, 2008, the disclosure of which is incorporated by reference herein. In addition or in the alternative, one button (516) may be operable to selectively restrict the degree to which cutter (150) may be retracted, thereby allowing the user to selectively define the effective length of lateral aperture (114). Examples of such operations are described in U.S. Pat. No. 7,517,322, entitled "Biopsy Device with Variable Side Aperture," issued Apr. 14, 2009, the disclosure of which is incorporated by reference herein. In some such versions, needle firing mechanism (400) may be rendered inoperable if cutter (150) is not allowed to retract far enough, while in some other versions needle firing mechanism (400) will remain fully operable even if cutter (150) is only allowed to retract slightly. In some versions where needle firing mechanism (400) remains fully operable despite receipt of user input to significantly restrict the retraction of cutter (150) (e.g., the user wishes to use a very short effective aperture (114), etc.), control module (510) may allow cutter (150) to retract as far as needed to provide operation of needle firing mechanism (400), then provide the user-specified limit on the retraction of cutter (150) during a cutting stroke/cycle after needle (110) has been fired.

By way of example only, buttons (516) may be configured and operable in accordance with any of the teachings of U.S. Non-Provisional patent application Ser. No. 12/542,775, entitled "Multi-Button Biopsy Device," filed Aug. 18, 2009, the disclosure of which is incorporated by reference herein. In versions where one button (516) is selectively assigned as the active button (516), one or more of LEDs (524) may be activated to provide a visual indication to the user showing which button (516) is active. As another merely illustrative variation, a button (516) that is selectively assigned as the active button (516) may be illuminated while the other buttons (516) remain non-illuminated. Other suitable ways in which buttons (516) may be provided an operable will be apparent to those of ordinary skill in the art in view of the teachings herein.

Tissue sample holder sensor (520) is operable to sense when tissue sample holder (300) is coupled with probe (100). Control module (510) may include a logic that prevents or restricts activation of motor (528) and/or other components of biopsy device (10) when tissue sample holder sensor (520) does not sense the presence of tissue sample holder (300) coupled with probe (100). In addition or in the alternative, during operation of biopsy device (10), when tissue sample holder (300) is removed from probe (100) in order to deposit a marker at a biopsy site using an applier fed through cutter lumen (154), control module (510) may include a logic that automatically retracts cutter (150) (or otherwise allows retraction of cutter (150)) proximally to effectively open lateral aperture (114) of needle (110) to allow the marker to be deployed at the biopsy site through lateral aperture (114). It should also be understood that control module (510) may be configured to rely on the presence of contact (380) as sensed by tissue sample holder sensor (520) to determine whether probe (100) is coupled with holster (500). For instance, holster (500) may remain in a powered-down state when tissue sample holder sensor (520) does not sense the presence of tissue sample holder (300) through contact (380). As soon as probe (100) and holster (500) are first coupled together, tissue sample holder sensor (520) may detect such coupling by sensing the presence of contact (380), and control module (510) may accordingly place holster (500) in a powered-on and/or idle state that is ready for full operation of biopsy device (10). Control module (510) may further be configured to at least substantially disable functioning of buttons (516) before tissue sample holder sensor (520) detects the coupling of probe (100) with holster (500). It should also be understood that control module (510) may react differently in a period before probe (100) is first coupled with holster (500) than it reacts in a period when tissue sample holder (300) is decoupled from probe (100) after probe (100) has been coupled with holster (500). For instance, holster (500) may remain at least substantially powered down in the first period while motor (528) may be activated to retract cutter (150) in the second period.

As noted above, tissue sample holder sensor (520) may comprise a metal contact that is configured and position to make contact with contact (380) of tissue sample holder (300) when holster (500) and probe (100) are coupled together. While sensor (520) and contact (380) make direct contact in this example, it should be understood that tissue sample holder sensor (520) may alternatively sense the presence of tissue sample holder (300) in a variety of other ways, including but not limited to using RFID, EE proms, or EAS technology. Furthermore, in some versions, tissue sample holder sensor (520) may be used to perform authenticity verification of tissue sample holder (500), permitting full operation of biopsy device (10) only when a properly authenticated tissue sample holder (300) is coupled with probe (100), and preventing at least some operation of biopsy device (10) when a non-authenticated tissue sample holder (300) is coupled with probe (100). Still other suitable ways in which a tissue sample holder sensor (520) may be configured an operable will be apparent to those of ordinary skill in the art in view of the teachings herein.

Speaker (522) and LEDs (524) may be used to provide various forms of feedback to a user operating biopsy device (10). As shown in FIG. 1, top housing (506) of holster (500) includes a plurality of speaker openings (508) to facilitate transmission of sound from speaker (522) to the user of biopsy device (10). While not shown in FIGS. 1-2, it should be understood that LEDs (524) may be positioned at any suitable locations on holster (500). In some versions, control module (510) is configured to communicate sound through speaker (522) and/or to illuminate/un-illuminate one or more LEDs (524) when an error condition is detected (e.g., battery (512) power low, drive mechanism jammed, motor current profile deviating from norm beyond acceptable range, motor rotation speed deviating from norm beyond acceptable range, etc.). In addition or in the alternative, control module (510) may be configured to communicate sound through speaker (522) and/or to illuminate/un-illuminate one or more LEDs (524) to indicate to the user which state of operation biopsy device (10) is in (e.g., cutter (150) at a distal position, cutter (150) being retracted, cutter (150) at a proximal position, cutter (150) being advanced, needle firing mechanism (400) loaded to point where arming slider (460) should be released, etc.). Various other suitable ways in which speaker (522) and/or LEDs (524) may be used will be apparent to those of ordinary skill in the art in view of the teachings herein. It should also be understood that speaker (522) and/or LEDs (524) may be substituted or supplemented with other user feedback features such as an LED display, etc.; and that speaker (522) and/or LEDs (524) may simply be omitted if desired.

As shown only in FIG. 12, holster (500) of the present example also includes a vacuum sensor (572). Vacuum sensor (572) is coupled with a sensor fitting (570), which is further coupled with vacuum port (566). Vacuum sensor (572) is thus configured to sense the level of vacuum that is provided by vacuum pump (560) and that is being communicated to tissue sample holder (300). Vacuum sensor (572) may comprise a diaphragm, a capacitive coupling, a strain gauge, or any other suitable device(s), component(s), or configurations. While not shown in FIG. 11, vacuum sensor (572) of the present example is in communication with control module (510), which may include a logic configured to process signals from vacuum sensor (572) and affect operation of biopsy device (10) accordingly. By way of example only, if vacuum sensor (572) indicates that the vacuum level within tissue sample holder (300) has not fallen below a predefined level (which may indicate that a tissue sample is lodged in aperture (114) and/or cutter lumen (154)), a "clear probe" algorithm may be initiated as described in at least one of the references cited herein. As another merely illustrative example, control logic (510) may be configured to initiate a cutting stroke by cutter (150) only after a vacuum level sensed by vacuum sensor (572) has fallen below a threshold. In addition or in the alternative, vacuum sensor (572) may be configured and/or used in accordance with any of the teachings in U.S. Pub. No. 2009/0171243, entitled "Vacuum Sensor and Pressure Pump for Tetherless Biopsy Device," published Jul. 2, 2009, the disclosure of which is incorporated by reference herein. Still other suitable ways in which vacuum sensor (572) may be configured and used will be apparent to those of ordinary skill in the art in view of the teachings herein. It should also be understood that, as with other components described herein, vacuum sensor (572) may be substituted, supplemented, or even omitted, as desired.

B. Exemplary Drive Components of Holster

Motor (528) of the present example comprises a conventional DC motor, though it should be understood that any other suitable type of motor may be used. By way of example only, motor (528) may comprise a pneumatic motor (e.g., having an impeller, etc.) that is powered by pressurized air, a pneumatic linear actuator, an electromechanical linear actuator, a piezoelectric motor (e.g., for use in MRI settings), or a variety of other types of movement-inducing devices. As mentioned above, motor (528) receives power from battery (512). While motor (528) is located onboard biopsy device (10) in the present example, it should be understood that motor (528) may instead be located some distance from biopsy device (10) and provide energy to biopsy device (10) via a drive shaft or cable, etc.

As also noted above, motor (528) is operable to drive cutter actuation mechanism (200). An exemplary drive train that may be coupled with motor (528) to drive cutter actuation mechanism (200) is shown in FIG. 12. In this example, the first end (530) of a main drive shaft extends distally from motor (528) while a second end (532) of the main drive shaft extends proximally from motor (528). An encoder wheel (534) is coupled with first end (530). Encoder wheel (534) is a conventional encoder wheel in this example, and includes a plurality of slots, openings, and/or tabs evenly spaced circumferentially at or near the outer periphery of encoder wheel (534). Encoder sensor (526) is positioned relative to encoder wheel (534) in a manner allowing encoder sensor (526) to track rotation of encoder wheel (534). Encoder sensor (526) is thus operable to track operation of motor (528). It should be understood that, with control module (510) being in communication with encoder sensor (526), encoder wheel (534), encoder sensor (526), and control module (510) may be used to gather data relating to the rotational speed and rotational position of first end (530), which may be processed to reflect the translation rate of cutter (150), the rotation rate (150) of cutter, the longitudinal position of cutter (150), etc. Such information may be used to control operation of other components of biopsy device (10), as described elsewhere herein or in other ways that will be apparent to those of ordinary skill in the art in view of the teachings herein.

First and second ends (530, 532) of the main drive shaft rotate simultaneously and in the same direction. A first gear (536) is secured to second end (532) of the main drive shaft, such that rotation of the main drive shaft when motor (528) is activated will also rotate first gear (536). First gear (536) is engaged with a second gear (538), which is secured to a second drive shaft (540). Accordingly, rotation of the main drive shaft is transmitted to second drive shaft (540) via meshing gears (536, 538). Second drive shaft (540) is fed into vacuum pump (560). Vacuum pump (560) of the present example comprises a conventional diaphragm pump. In particular, second drive shaft (540) is coupled with an eccentric disk (not shown—e.g., a device for converting circular motion into rectilinear motion, comprising a disk fixed off-center to second shaft (540), etc.), which is configured to cause a rod (not shown—e.g., the rod may be coupled with or otherwise driven by the eccentric disk, etc.) of vacuum pump (560) to reciprocate as motor (528) rotates second drive shaft (540). This rod of vacuum pump (560) drives a diaphragm (not shown) of vacuum pump (560) as the rod reciprocates, causing vacuum pump (560) to induce a vacuum. It should be understood that vacuum pump (560) of the present example operates in the same way regardless of which direction motor (528) rotates. Of course, any other suitable type of vacuum pump may be used.

Vacuum pump (560) of the present example includes a port (562) that is coupled with a conduit (564), which is further coupled with vacuum port (566). Vacuum pump (560) is thus operable to draw a vacuum through vacuum port (566) via port (562) and conduit (564) when motor (528) rotates second drive shaft (540). As noted above, primary vacuum port (340) is configured to couple with vacuum port (566) when holster (500) and probe (100) are coupled together. It should therefore be understood that vacuum pump (560) is operable to induce a vacuum in tissue sample holder (300) when motor (528) rotates second drive shaft (540) when holster (500) and probe (100) are coupled together. The term "vacuum" as used herein should read broadly to include suction in general (e.g., any pressure below atmospheric pressure), and should not be read as necessarily requiring a pressure level of exactly zero or a negative pressure level, etc. As noted above, vacuum pump (560) may be assisted with or replaced by an external vacuum source that is coupled with secondary vacuum port (350) of tissue sample holder (300). Other suitable forms that vacuum pump (560) may take, as well as other suitable ways in which a vacuum pump (560) may be operated, will be apparent to those of ordinary skill in the art in view of the teachings herein. Alternatively, biopsy device (10) may be configured to operate without a vacuum pump.

A third gear (542) is also secured to second drive shaft (540), and rotates unitarily therewith. Third gear (542) meshes with a fourth gear (544), which is secured to a third drive shaft (546). Accordingly, rotation of the main drive shaft is transmitted to third drive shaft (546) via meshing gears (536, 538, 542, 544) and second drive shaft (540). A fifth gear (548) is also secured to third drive shaft (546), and rotates unitarily therewith. Fifth gear (548) meshes with a sixth gear (550), which is secured to a fourth drive shaft (552). Sixth gear (554) is also secured to fourth drive shaft (552) and rotates unitarily therewith. Accordingly, rotation of the main drive shaft is transmitted to gears (550, 554) via meshing gears (536, 538, 542, 544, 548, 554) and drive shafts (540, 546, 552). Drive shafts (540, 546, 552) are supported by various bearings (556) that are coaxially disposed about drive shafts (540, 546, 552). Gears (550, 554) are exposed through an opening formed through chassis (504) of holster (500), and are configured to mesh with gears (202, 204) exposed through chassis (120) of probe (100) as described above. Motor (528) is thus able to rotatingly drive cutter actuation mechanism (200) of probe (100) through meshing of gears (550, 554, 202, 204) when probe (100) and holster (500) are coupled together. Of course, a variety of other components or configurations may be used to provide a coupling between motor (528) and cutter (150), in addition to or in lieu of any or all of those drive components described above.

In some versions, holster (500) includes one or more headlights (not shown) that are operable to illuminate an insertion area for needle (110). Examples of such use of headlights are disclosed in U.S. Pub. No. 2008/0214955, entitled "Presentation of Biopsy Sample by Biopsy Device," published Sep. 4, 2008, the disclosure of which is incorporated by reference herein. In addition or in the alternative, holster (500) may include a laser light source that is operable to project a laser beam to assist in targeting for needle (110). Various examples of such a use of a laser are disclosed in U.S. Pub. No. 2010/0106056, entitled "Methods for Medical Device Alignment," published Apr. 29, 2010, the disclosure of which is incorporated by reference herein. Still other suitable components, features, configurations, and operabilites that may be incorporated into holster (500), for driving cutter actuation mechanism (200) or otherwise, will be apparent to those of ordinary skill in the art in view of the teachings herein.

V. Exemplary Alternative Versions

Figure 13:
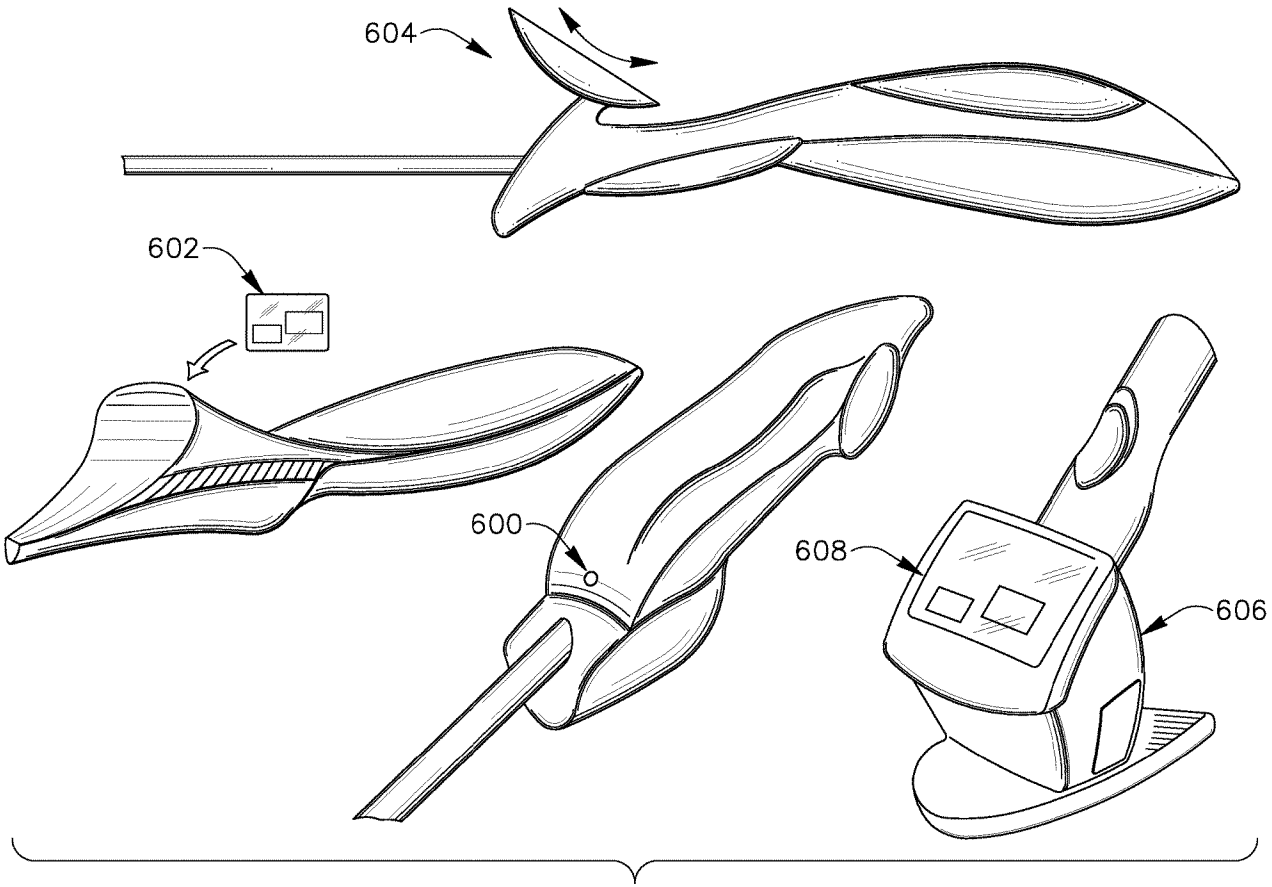
FIG. 13 depicts various views of exemplary alternative versions of the biopsy device of FIG. 1.

FIG. 13 depicts various exemplary alternative versions of biopsy device (10). For instance, FIG. 13 depicts a version of a biopsy device having a laser light source (600) as mentioned above. FIG. 13 also depicts a version of a biopsy device having a fixed graphical display (602); as well as a version of a biopsy device having a tilting graphical display (604). In addition, FIG. 13 depicts a biopsy device disposed in a docking station (606), with docking station (606) having a graphical display (608). It should be understood that any of these features, among others, may be readily incorporated into biopsy device described above, as well as any other type of biopsy device.

Figure 14:
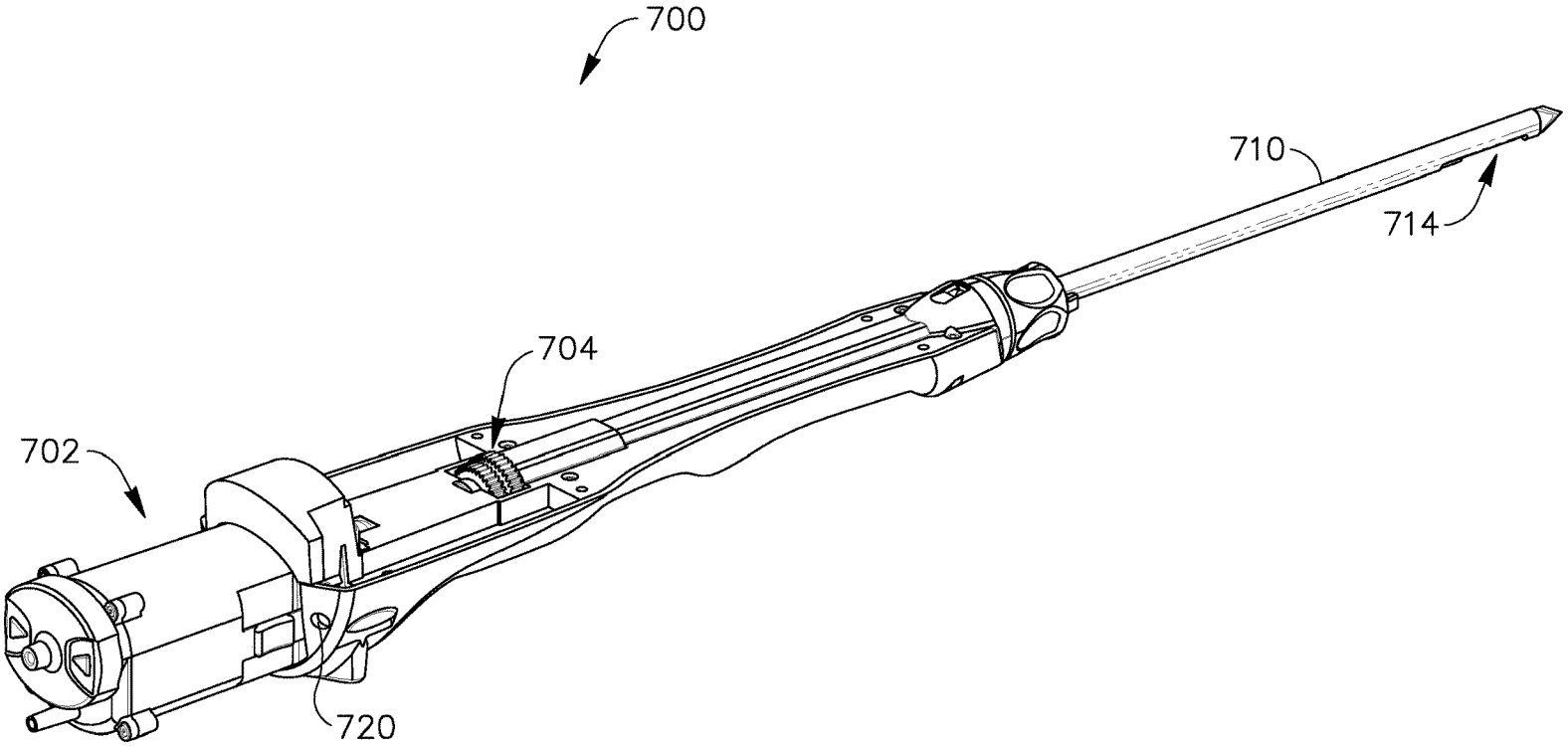
FIG. 14 depicts a perspective view of an exemplary alternative biopsy probe.
Figure 15:
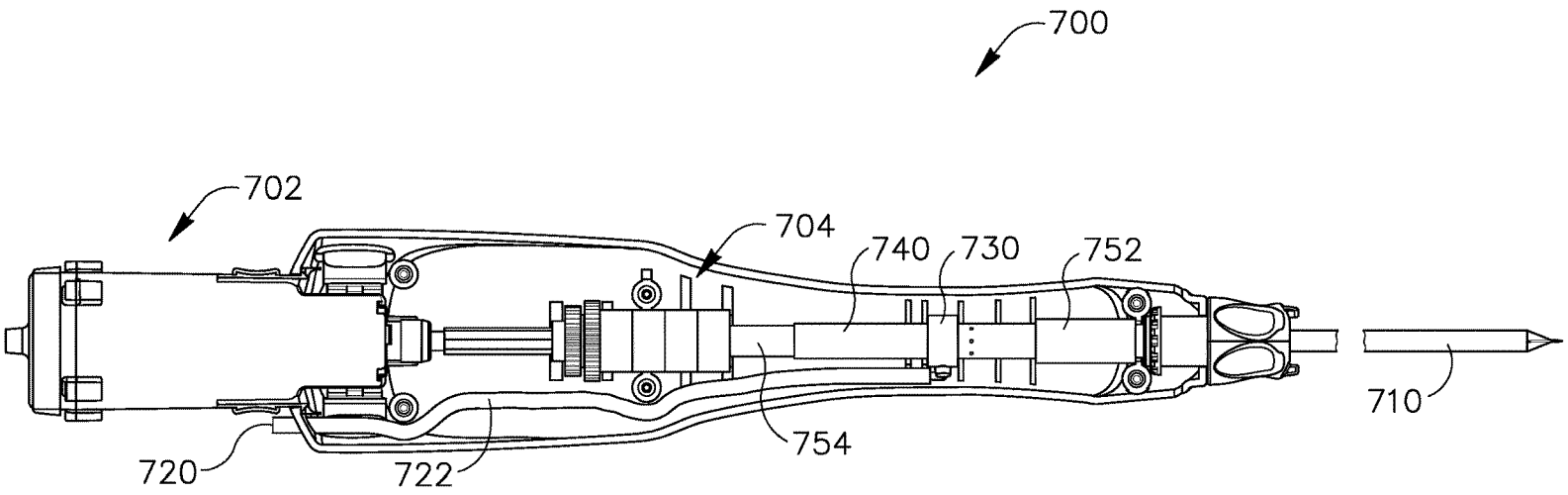
FIG. 15 depicts a top plan view of the probe of FIG. 14, with a top chassis removed.

FIGS. 14-15 show another exemplary biopsy probe (700), which may be coupled with holster (500) just like probe (100) described above. Unless otherwise indicated herein, components of probe (700) in this example are substantially identical to components of probe (100) described above. For instance, probe (700) of this example includes a tissue sample holder (702) that is substantially identical to tissue sample holder (300) described above. Similarly, probe (700) of this example includes a cutter actuation mechanism (704) that is substantially identical to cutter actuation mechanism (200) described above. In probe (700), however, there is no needle firing mechanism (400), though it should be understood that probe (700) may alternatively have a needle firing mechanism (400) (or variation thereof), if desired.

Probe (700) of the present example also includes a needle (710) that is larger than needle (110) of biopsy device (10). For instance, needle (710) may have a size of approximately 8 gauge; with needle (110) having a size of approximately 13 gauge. Needle (710) of this example is otherwise configured the same as needle (110) described above. In some uses of a needle having such a relatively large size, there may be an increased risk of excess bleeding when a relatively large sized needle (710) is inserted into tissue. In some instances, such excess bleeding may present risks that the biopsy device might malfunction, such as due to coagulation of the excess blood on moving parts of the device, etc. Accordingly, probe (700) of the present example includes a port (720) for communicating saline through needle (710), to facilitate flushing of any excess blood. In some versions, port (720) is coupled with a source of pressurized saline. In some other versions, port (720) is coupled with a source of saline that is positioned vertically higher than biopsy probe (700), such that saline is fed into port (720) by gravity. In addition or in the alternative, saline may simply be drawn through port (720) from a saline source by a vacuum induced by vacuum pump (560) through the inner lumen [(754)] (*755*) of cutter (750).

Figure 17:
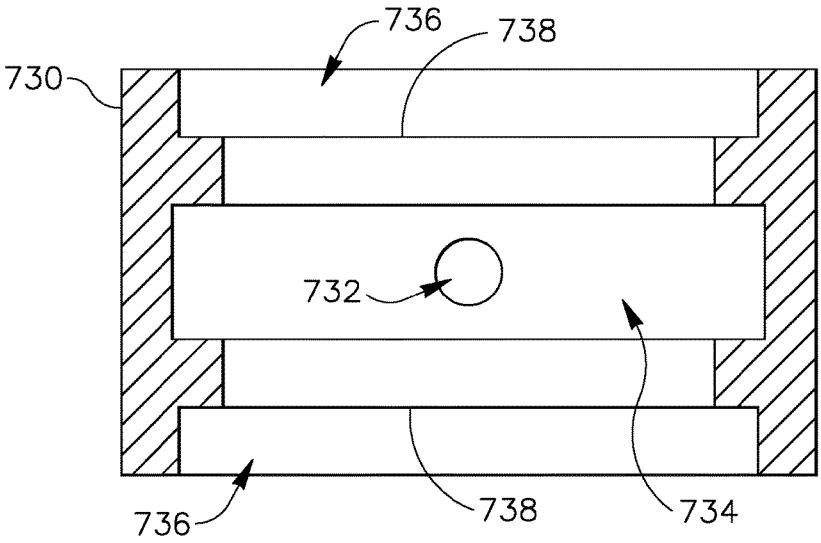
FIG. 17 depicts a side cross-sectional view of a saline manifold of the valving components of FIG. 16.

As shown in FIG. 15, probe (710) also includes a conduit (722) that couples port (720) with a port (732) in a saline manifold (730). As shown in FIG. 17, port (732) communicates with an interior region (734) of saline manifold (730). A pair of exterior regions (736) are on opposite sides of interior region (734), and are separated from interior region (734) by annular walls (738). A respective o-ring (not shown) is positioned in each exterior region (736), providing a substantial seal for annular walls (738). In other words, saline communicated to interior region (734) will not leak out into exterior regions (736) when saline manifold (730) is disposed about a valve sleeve (740) as described in greater detail below.

Figure 16:
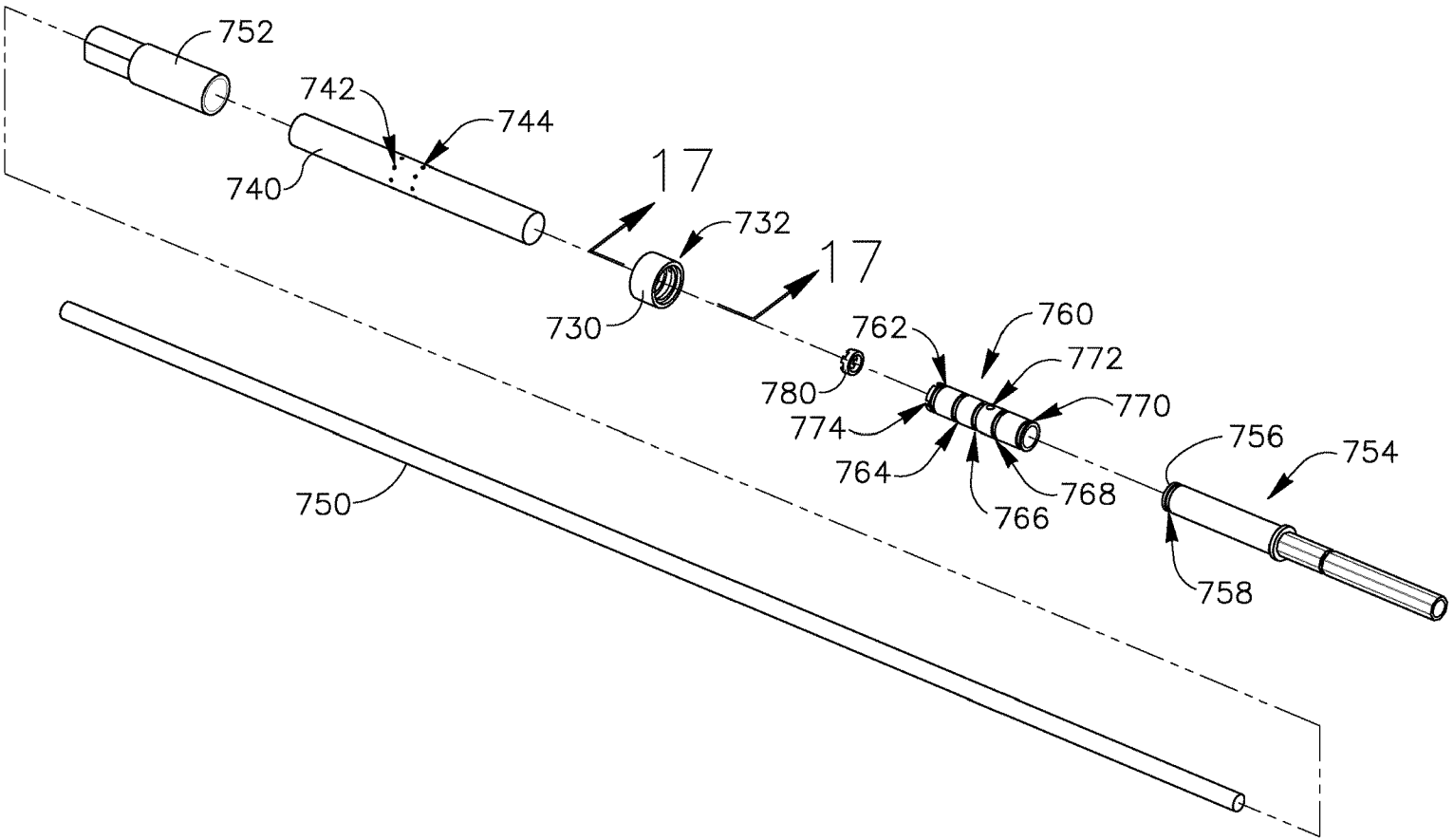
FIG. 16 depicts an exploded perspective view of valving components of the probe of FIG. 15.

As shown in FIG. 16, various valving components are coaxially disposed about cutter (750) of probe (700). In particular, a needle manifold (752) is located distal to other valving components. Needle overmold (752) is coupled with needle (710) in a manner similar to the coupling of needle overmold (410) with needle (110) described above. Cutter overmold (754) is coupled with cutter (750) in a manner similar to the coupling of cutter overmold (210) with cutter (150) as described above. Cutter overmold (754) is also configured similar to cutter overmold (210), except that cutter overmold (754) of this example lacks distal flange (216). Cutter overmold (754) includes a distal end (756) and an annular recess (758) just proximal to distal end (756). Annular recess (758) is configured to receive an o-ring (not shown).

Saline manifold (730) is coaxially positioned about valve sleeve (740). Valve sleeve (740) is inserted into the proximal end of needle overmold (752) such that the interior of valve sleeve (740) communicates with a second lumen (not shown) of needle (710), similar to communication of the interior of vent sleeve (420) with second lumen (168) of needle (710). Valve sleeve (740) is secured unitarily to needle overmold (752). Unlike vent sleeve (420), valve sleeve (740) does not translate within probe (710) in this example (e.g., since needle (710) cannot be fired in this example). Valve sleeve (740) includes a distal set of openings (742) and a proximal set of openings (744). Saline manifold (730) is positioned along the length of valve sleeve (740) at a location where interior region (734) is in fluid communication with proximal openings (744). This position and relationship of saline manifold (730) and valve sleeve (740) stays constant during operation of probe (710).

A shuttle valve slider (760) is coaxially positioned within valve sleeve (740), and is configured to translate in response to actuation of cutter (750). Shuttle valve slider (760) includes first, second, third, fourth, and fifth annular recesses (762, 764, 766, 768, 770). Each annular recess (762, 764, 766, 768, 770) is configured to receive a respective o-ring (not shown) to seal against the inner surface of valve sleeve (740). Shuttle valve slider (760) is similar in this respect to shuttle valve slider (430) described above. Shuttle valve slider (760) also includes a transverse opening (772), which is configured to selectively communicate with distal openings (742), communicate with proximal openings (744), or be substantially sealed relative to either set of openings (742, 744), depending on the longitudinal position of shuttle valve slider (760) in valve sleeve (740). Transverse opening (772) is longitudinally positioned between third and fourth annular recesses (766, 768).

An annular stop member (780) is unitarily secured to cutter (150) by a friction fit, and is configured to engage the distal end of shuttle valve slider (760) as cutter (750) is moved proximally and thereby push shuttle valve slider (760) proximally relative to valve sleeve (740). Shuttle valve slider (760) may be pushed distally by distal end (756) of cutter overmold (754) when cutter (750) is moved distally.

Like shuttle valve slider (430), shuttle valve slider (760) of the present example defines an inner diameter that is greater than the outer diameter defined by cutter (750), such that a longitudinally extending gap (751) is provided between the outer diameter of cutter (750) and the inner diameter of shuttle valve slider (760). Such a gap (751) is sufficient to provide longitudinal fluid communication (e.g., atmospheric air, saline, etc.) between the outer diameter of cutter (750) and the inner diameter of shuttle valve slider (760). In addition, the distal end of shuttle valve slider (760) include notches (774) formed therein, providing an appearance similar to that of a castellated nut or castle nut.

As noted above, translation of cutter (750) provides translation of shuttle valve slider (760) due to engagement between either annular stop member (780) and the distal end of shuttle valve slider (760) or distal end (756) of cutter overmold (754) and the proximal end of shuttle valve slider (760). The distance separating annular stop member (780) and distal end (756) of cutter overmold (754), even when cutter (750) is at a distal-most position, is greater than the length of shuttle valve slider (760). Thus, like with shuttle valve slider (430) as described above, there is some degree of "lost motion" between shuttle valve slider (760) and cutter (750) as cutter (750) translates in either direction. It should be understood that shuttle valve slider (760) may be located at various positions within valve sleeve (740) during various stages of translation of cutter (750). In particular, shuttle valve slider (760) may be located at positions where distal openings (742) are positioned between one pair of annular recesses (762, 764, 766, 768, 770) and their corresponding o-rings; with proximal openings (744) being positioned between another pair of annular recesses (762, 764, 766, 768, 770) and their corresponding o-rings. In some versions, shuttle valve slider (760) may travel to a proximal-most position (FIG. 18A), whereby distal openings (742) are positioned proximal to first annular recess (762) and its o-ring and distal to second annular recess (764) and its o-ring. In addition or in the alternative, shuttle valve slider (760) may travel to a distal-most position (FIG. 18B), whereby proximal openings (744) are positioned proximal to fourth annular recess (768) and its o-ring and distal to fifth annular recess (770) and its o-ring.

Figure 19A:
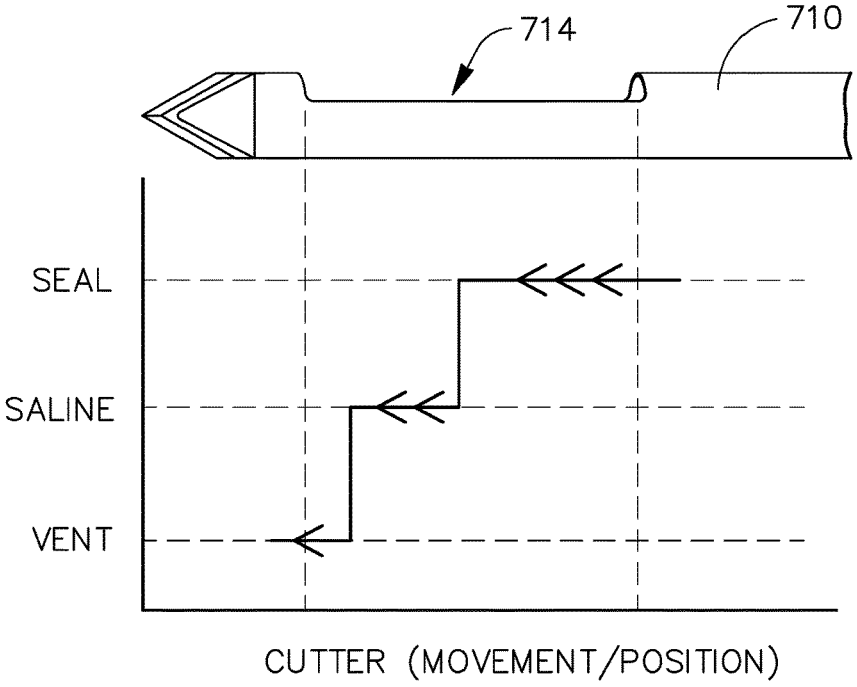
FIG. 19A depicts a schematic view of exemplary communicative states for a second lumen of the needle of the probe of FIG. 15, in relation to the longitudinal position of the cutter within the needle, during advancement of the cutter from a proximal position to a distal position.
Figure 19B:
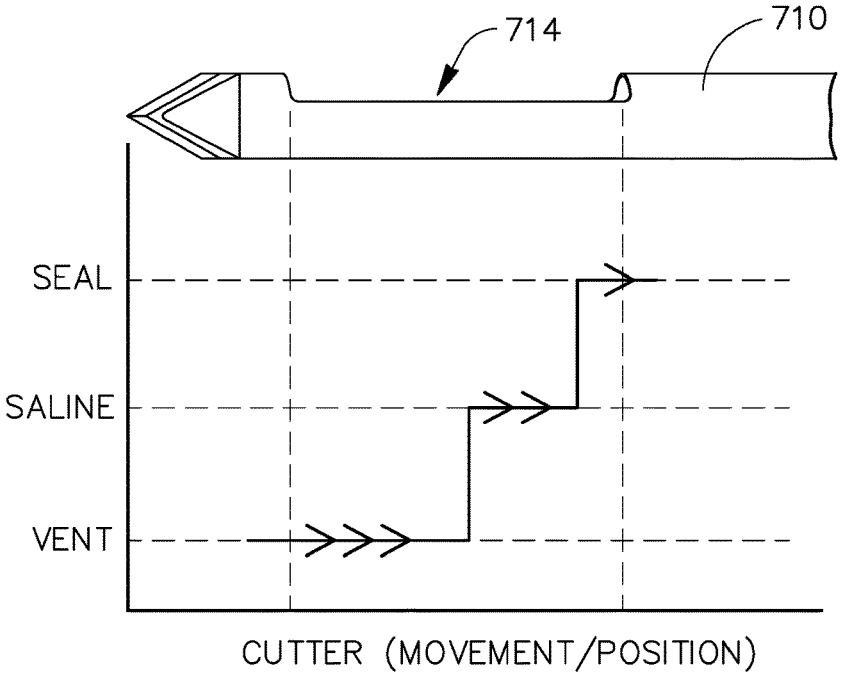
FIG. 19B depicts a schematic view of exemplary communicative states for a second lumen of the needle of the probe of FIG. 15, in relation to the longitudinal position of the cutter within the needle, during retraction of the cutter from a distal position to a proximal position.

In configurations where shuttle valve slider (760) is positioned such that distal openings (742) are positioned between first and second annular recesses (762, 764) and their corresponding o-rings (see FIG. 18A), between second and third annular recesses (764, 766) and their corresponding o-rings, or between fourth and fifth annular recesses (768, 770) and their corresponding o-rings, the interior of valving sleeve (740) (and, hence, the second lumen of needle (710)) is substantially sealed relative to atmospheric air. However, in configurations or stages of operation where shuttle valve slider (760) is positioned such that distal openings (742) are positioned between third and fourth annular recesses (766, 768) and their corresponding o-rings, as shown in FIG. 18B, the interior of valving sleeve (740) (and, hence, the second lumen of needle (710)) is in communication with atmospheric air via distal openings (742) and transverse opening (772). In some versions of probe (700), the actual range of travel for shuttle valve slider (760) does not include all of these longitudinal positions. FIG. 19A shows the range of cutter (750) travel where the second lumen of needle (710) is vented by shuttle valve slider (760) and distal openings (742) during distal advancement of cutter (750) in the present example; while FIG. 19B shows the range of cutter (750) travel where the second lumen of needle (710) is vented by shuttle valve slider (760) and distal openings (742) during proximal retraction of cutter (750) in the present example.

Similarly, in configurations where shuttle valve slider (760) is positioned such that proximal openings (744) are positioned between first and second annular recesses (762, 764) and their corresponding o-rings, between second and third annular recesses (764, 766) and their corresponding o-rings (see FIG. 18A), or between fourth and fifth annular recesses (768, 770) and their corresponding o-rings (see FIG. 18B), the interior of valving sleeve (740) (and, hence, the second lumen of needle (710)) is substantially sealed relative to saline from saline manifold (730). However, in configurations where shuttle valve slider (760) is positioned such that proximal openings (744) are positioned between third and fourth annular recesses (766, 768) and their corresponding o-rings, the interior of valving sleeve (740) (and, hence, the second lumen of needle (710)) is in communication with saline from saline manifold (730) via proximal openings (744) and transverse opening (772). Again, in some versions of probe (700), the actual range of travel for shuttle valve slider (760) does not include all of these longitudinal positions. FIG. 19A shows the range of cutter (750) travel where saline is provided to the second lumen of needle (710) by shuttle valve slider (760) and proximal openings (744) during distal advancement of cutter (750) in the present example; while FIG. 19B shows the range of cutter (750) travel where saline is provided the second lumen of needle (710) by shuttle valve slider (760) and proximal openings (744) during proximal retraction of cutter (750) in the present example.

It should also be understood that shuttle valve slider (760) may be located at longitudinal positions where neither saline nor atmospheric air is communicated to the interior of valving sleeve (740) (and, hence, the second lumen of needle (710)). For instance, shuttle valve slider may be located at a position where distal openings (742) are located between first and second annular recesses (762, 764) and their corresponding o-rings; with proximal openings (744) being located between second and third annular recesses (764, 766) and their corresponding o-rings. In such a configuration, as shown in FIG. 18A, the interior of valving sleeve (740) (and, hence, the second lumen of needle (710)) is substantially sealed relative to both atmosphere and saline manifold (730). FIG. 19A shows the range of cutter (750) travel the second lumen of needle (710) is substantially sealed by shuttle valve slider (760) during distal advancement of cutter (750) in the present example; while FIG. 19B shows the range of cutter (750) travel the second lumen of needle (710) is substantially sealed by shuttle valve slider (760) during proximal retraction of cutter (750) in the present example.

Various stages of actuation of cutter (750) at which any of the above-noted fluid communication states for the interior of valving sleeve (740) (and, hence, the second lumen of needle (710)) may apply will be apparent to those of ordinary skill in the art in view of the teachings herein. An exemplary algorithm is shown in FIGS. 19A-19B, which depicts the fluid communication state of the second lumen of needle (710) as cutter (750) moves in relation to the lateral aperture (714) of needle (710). The solid line in the field of the charts shown in FIGS. 19A-19B represents the position of the distal end of cutter (750) during translation of cutter (750) within needle (710). In addition, the arrowheads in FIGS. 19A-19B simply indicate the direction in which cutter (750) is moving (not necessarily the direction in which fluid is flowing).

In the present example, with cutter (750) fully retracted to a proximal position, shuttle valve slider (760) is in a proximal position as shown in FIG. 18A. As shown in FIG. 19A, the second lumen of needle (710) is thus initially sealed (relative to atmosphere and saline) as cutter (750) begins advancing from the proximal position to a distal position. During the initial stages of cutter (750) advancement, the second lumen of needle (710) remains sealed by shuttle valve slider (760). As cutter (750) begins approaching a distal position, but before cutter (750) effectively closes lateral aperture (714), cutter overmold (754) eventually engages shuttle valve slider (760) and begins to push shuttle valve slider (760) distally, such that the second lumen of needle (710) eventually receives saline through openings (744, 772) and gap (751). With suction being applied to the inner lumen [(754)] (*755*) of cutter (752), such saline (along with blood, etc., from the biopsy site) may be drawn proximally through inner lumen [(754)] (*755*) of cutter (752), such that the saline, etc., will ultimately be communicated to tissue sample holder (702). As cutter (750) continues to advance distally, cutter overmold (754) continues to push shuttle valve slider (760) distally, such that the second lumen of needle (710) is eventually vented by receiving atmospheric air through openings (742, 772) and gap (751). When cutter (750) reaches a distal-most position, as shown in FIG. 18B, the second lumen of needle (710) continues to be vented. It should be understood that, with a suction being applied proximally through inner lumen [(754)] (*755*) of cutter (750), and with a vent being applied to the second lumen of needle (710), the resulting pressure differential will provide communication of tissue samples proximally through inner lumen [(754)] (*755*) of cutter (750), ultimately depositing the severed tissue samples into tissue sample holder (702).

As shown in FIG. 19B, as cutter (750) is initially retracted from a distal position (FIG. 18B) to a proximal position (FIG. 18A) in the present example, the second lumen of needle (710) is vented to atmosphere via openings (742, 772) and gap (751). As cutter (750) continues to retract proximally, stop member (780) eventually engages shuttle valve slider (760) and pushes shuttle valve slider (760) proximally, such that the second lumen of needle (710) eventually receives saline via openings (742, 744) and gap (751). While cutter (750) continues to retract further proximally, shuttle valve slider (750) eventually moves to a proximal position shown in FIG. 18A, where shuttle valve slider (750) substantially seals the second lumen of needle (710) (relative to atmosphere and relative to saline). Of course, the communicative states for the second lumen of needle (710) and their relation to the movement/position of cutter (750) described above are mere examples. Various other suitable communicative states for the second lumen of needle (710) and their relation to the movement/position of cutter (750) will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, comprising:

(a) a body;

(b) a needle, the needle including a tip and a transverse aperture proximal to the tip, wherein the needle defines a longitudinal axis, wherein the needle is movable relative to the body along the longitudinal axis;

(c) a cutter movable within the needle to sever tissue protruding through the transverse aperture, wherein the cutter comprises a first member fixedly secured to the cutter;

(d) a motor operable to move the cutter relative to the needle;

(e) a needle firing assembly comprising a second member, wherein the motor is further operable to actuate the needle firing assembly to retract and fire the needle relative to the body along the longitudinal axis, wherein the second member of the needle firing assembly is configured to engage the first member of the cutter, wherein the needle firing assembly is operable to retract the needle relative to the body along the longitudinal axis when at least the following two conditions are met:

(i) the second member is engaged with the first member, and (ii) the motor is activated to retract the cutter proximally relative to the body.

2. The biopsy device of claim 1, wherein the needle firing assembly is configured to engage the cutter to retract the needle proximally with the cutter as the cutter is retracted from a first distal position to a first proximal position.

3. The biopsy device of claim 2, wherein the needle firing assembly is configured to fire the needle distally when the cutter is advanced from the first proximal position to a second distal position, wherein the second distal position is proximal to the first distal position.

4. The biopsy device of claim 3, wherein the cutter is further movable from the second distal position to a second proximal position after the needle is fired distally, wherein the second proximal position is proximal to the first proximal position.

5. The biopsy device of claim 1, wherein the second member comprises an elongate member resiliently biased to assume a bent configuration, wherein the second member is disengaged from the first member when the elongate member is in the bent configuration, wherein the second member is engaged with the first member when the elongate member is moved toward a straight configuration, the needle firing assembly further comprising a trigger member operable to move the elongate member from the bent configuration toward the straight configuration.

6. The biopsy device of claim 1, wherein the body includes a track, wherein the second member comprises a pin disposed in the track, wherein the track is configured to maintain engagement between the first member and the second member as the pin moves along a first portion of the track, wherein the track is configured to permit disengagement of the first member from the second member as the pin moves along a second portion of the track.

7. The biopsy device of claim 1, wherein the first member includes an outwardly extending flange, wherein the second member includes an inwardly extending catch configured to selectively engage the flange.

8. The biopsy device of claim 1, wherein the longitudinal axis defined by the needle passes through the body.

9. The biopsy device of claim 1, wherein the motor is positioned within the body.

10. A biopsy device, comprising:

(a) a body;

(b) a needle extending distally from the body, the needle including a tip and a transverse aperture proximal to the tip, wherein the needle defines a longitudinal axis, [wherein the needle is translatable relative to the body along the longitudinal axis,] wherein the needle is selectively rotatable relative to the body about the longitudinal axis;

(c) a cutter movable relative to the needle to sever tissue protruding through the transverse aperture; and (d) a needle rotation assembly, *wherein the needle rotation assembly comprises a locking portion,* wherein the needle rotation assembly is configured to prevent rotation of the needle about the longitudinal axis when the [needle] *locking portion* is in a first longitudinal position relative to the body, wherein the needle rotation assembly is further configured to permit rotation of the needle about the longitudinal axis when the [needle] *locking portion* is in a second longitudinal position relative to the body.

11. The biopsy device of claim 10, wherein the needle rotation assembly comprises a resilient member resiliently biasing the [needle] *locking portion* to the first longitudinal position, wherein the first longitudinal position is proximal to the second longitudinal position.

12. The biopsy device of claim 10, [wherein the needle rotation assembly further comprises a needle rotation member unitarily secured to the needle,] wherein the body comprises a needle engagement feature configured and positioned to engage the [needle rotation member] *locking portion* when the [needle] *locking portion* is in the first longitudinal position to substantially prevent rotation of the needle about the longitudinal axis, wherein the needle engagement feature is configured and positioned to disengage the [needle rotation member] *locking portion* when the [needle] *locking portion* is in the second longitudinal position to permit rotation of the needle about the longitudinal axis.

13. The biopsy device of claim 12, wherein the needle engagement feature comprises a protrusion projecting from an interior surface of the body, wherein the [needle rotation member] *locking portion* comprises a plurality of recesses circumferentially arrayed about an outer perimeter of the [needle rotation member] *locking portion*, wherein each of the recesses is configured to receive part of the protrusion based on the angular position of the recesses about the longitudinal axis when the [needle] *locking portion* is in the first longitudinal position.

14. A biopsy device, comprising:

(a) a body;

(b) a needle, the needle including a tip and a transverse aperture proximal to the tip, wherein the needle defines a longitudinal axis, wherein the needle is movable relative to the body along the longitudinal axis;

(c) a cutter movable within the needle to sever tissue protruding through the transverse aperture;

(d) a first member, wherein the first member is fixedly secured to the cutter;

(e) a needle firing assembly, wherein the needle firing assembly is operable to retract and fire the needle relative to the body along the longitudinal axis, the needle firing assembly comprising a second member, wherein the second member is configured to selectively engage the first member; and (f) a motor operable to move the cutter relative to the needle, wherein the motor is further operable to actuate the needle firing assembly to retract and fire the needle relative to the body along the longitudinal axis, wherein the needle firing assembly is operable to retract the needle relative to the body along the longitudinal axis when at least the following two conditions are met:

(i) the second member is engaged with the first member, and (ii) the motor is activated to retract the cutter proximally relative to the body.

15. The biopsy device of claim 14, wherein the second member comprises an elongate member resiliently biased to assume a bent configuration, wherein the second member is disengaged from the first member when the elongate member is in the bent configuration, wherein the second member is engaged with the first member when the elongate member is in a substantially straight configuration, the needle firing assembly further comprising a trigger member operable to move the elongate member from the bent configuration to the substantially straight configuration.

16. The biopsy device of claim 14, wherein the body includes a track, wherein the second member comprises a pin disposed in the track, wherein the track is configured to maintain engagement between the first member and the second member as the pin moves along a first portion of the track, wherein the track is configured to permit disengagement of the first member from the second member as the pin moves along a second portion of the track.

17. The biopsy device of claim 14, wherein the first member includes an outwardly extending flange, wherein the second member includes an inwardly extending catch configured to selectively engage the flange.

18. The biopsy device of claim 14, wherein the longitudinal axis defined by the needle passes through the body.

19. The biopsy device of claim 14, wherein the motor is positioned within the body.

20. The biopsy device of claim 14, wherein the motor is positioned outside of the body.

*21. The biopsy device of claim 10, wherein the needle rotation assembly further comprises a rotation knob, wherein the locking portion comprises a rotation hub.*

*22. The biopsy device of claim 21, wherein the rotation hub and rotation knob are configured to rotate and translate together unitarily relative to the longitudinal axis defined by the needle.*

*23. The biopsy device of claim 22, wherein the rotation hub and the rotation knob are resiliently biased toward the first longitudinal position.*

*24. The biopsy device of claim 21, further comprising a needle overmold, wherein the needle overmold is unitarily secured to the needle.*

*25. The biopsy device of claim 24, wherein the needle overmold is engaged with the rotation hub such that the rotation hub is operable to rotate the needle overmold to thereby rotate the needle.*

*26. The biopsy device of claim 24, wherein the rotation hub is configured to translate relative to the needle overmold.*

*27. The biopsy device of claim 24, wherein the needle overmold is slidably disposed coaxially within the rotation hub.*

*28. A biopsy device, comprising:*

(*a*) *a body;*

(*b*) *a needle extending distally from the body, the needle including a tip and a transverse aperture proximal to the tip, wherein the needle defines a longitudinal axis, wherein the needle is rotatable relative to the body about the longitudinal axis;*

(*c*) *a cutter movable relative to the needle to sever tissue protruding through the transverse aperture; and*

(*d*) *a needle hub, wherein the needle hub is movable longitudinally relative to the body between a first longitudinal position and a second longitudinal position, wherein the needle hub is configured to prevent rotational movement of the needle when the needle hub is in the first longitudinal position relative to the body, wherein the needle hub is further configured to permit rotational movement of the needle when the needle hub is in the second longitudinal position relative to the body.*

*29. The biopsy device of claim 28, further comprising a resilient member and a rotation knob engaged with the needle hub, wherein the rotation knob is operable to drive rotation of the needle hub.*

*30. The biopsy device of claim 29, wherein the rotation knob is configured to translate unitarily with the needle hub, wherein the resilient member is configured to resiliently bias the rotation knob and the needle hub to the first longitudinal position.*

*31. The biopsy device of claim 28, wherein the needle hub comprises a proximal flange, wherein the proximal flange includes a plurality of locking features, wherein at least one locking feature of the plurality of locking features is configured to engage a portion of the body in response to the needle hub being located in the first longitudinal position.*

*32. The biopsy device of claim 28, wherein the at least one locking feature of the plurality of locking features is configured to disengage the portion of the body in response to the needle hub being located in the second longitudinal position.*

*33. The biopsy device of claim 28, wherein the first longitudinal position is proximal to the second longitudinal position.*

*34. The biopsy device of claim 28, wherein the needle hub is configured to translate relative to the needle between the first and second longitudinal positions.*

*35. The biopsy device of claim 28, wherein the needle is configured to rotate with the needle hub about the longitudinal axis when the needle hub is in the second longitudinal position.*

* * * * *